United States Patent
Davis et al.

(10) Patent No.: US 12,257,060 B2
(45) Date of Patent: Mar. 25, 2025

(54) METHODS AND SYSTEMS FOR PREDICTING ARRHYTHMIA RISK UTILIZING MACHINE LEARNING MODELS

(71) Applicant: Pacesetter, Inc., Sylmar, CA (US)

(72) Inventors: Kevin Davis, Thousand Oaks, CA (US); Aditya Goil, Stevenson Ranch, CA (US)

(73) Assignee: Pacesetter, Inc., Sylmar, CA (US)

( * ) Notice: Subject to any disclaimer, the term of this patent is extended or adjusted under 35 U.S.C. 154(b) by 523 days.

(21) Appl. No.: 17/554,745

(22) Filed: Dec. 17, 2021

(65) Prior Publication Data

US 2022/0304612 A1    Sep. 29, 2022

Related U.S. Application Data

(60) Provisional application No. 63/167,213, filed on Mar. 29, 2021.

(51) Int. Cl.
| | | |
|---|---|---|
| A61B 5/00 | (2006.01) |
| A61B 5/283 | (2021.01) |
| A61B 5/352 | (2021.01) |
| A61B 5/353 | (2021.01) |
| A61B 5/358 | (2021.01) |
| A61B 5/363 | (2021.01) |

(Continued)

(52) U.S. Cl.
CPC ............ *A61B 5/363* (2021.01); *A61B 5/0006* (2013.01); *A61B 5/283* (2021.01); *A61B 5/352* (2021.01); *A61B 5/353* (2021.01); *A61B 5/358* (2021.01); *A61B 5/366* (2021.01); *A61B 5/389* (2021.01); *A61B 5/686* (2013.01); *A61B 5/7267* (2013.01); *A61B 5/7275* (2013.01); *A61B 5/746* (2013.01)

(58) Field of Classification Search
CPC ....... A61B 5/363; A61B 5/0006; A61B 5/283; A61B 5/352; A61B 5/353; A61B 5/358; A61B 5/366; A61B 5/389; A61B 5/686; A61B 5/7267; A61B 5/7275; A61B 5/746
See application file for complete search history.

(56) References Cited

U.S. PATENT DOCUMENTS

| 7,272,435 B2 | 9/2007 | Rowlandson |
| 8,244,654 B1 | 8/2012 | Hobgood et al. |

(Continued)

FOREIGN PATENT DOCUMENTS

| EP | 2194865 A1 | 6/2010 |
| EP | 2347266 A1 | 7/2011 |

(Continued)

*Primary Examiner* — Scott M. Getzow
(74) *Attorney, Agent, or Firm* — Dean D. Small; The Small Patent Law Group, LLC

(57) ABSTRACT

A system and method for determining an arrhythmia risk are provided and include memory to store specific executable instructions and a machine learning (ML) model trained to predict an arrhythmia with a characteristic of interest (COI) that exhibits a non-physiologic behavior. One or more processors are configured to execute the specific executable instructions to obtain CA signals collected by an implantable medical device (IMD), wherein the COI exhibits a physiologic behavior and apply the ML model to the CA signals to identify a risk factor that a patient will experience the arrhythmia at a future point in time even though the COI in the CA signals, exhibits a physiologic behavior.

22 Claims, 5 Drawing Sheets

(51) Int. Cl.
*A61B 5/366* (2021.01)
*A61B 5/389* (2021.01)

(56) References Cited

U.S. PATENT DOCUMENTS

| | | |
|---|---|---|
| 8,319,648 B2 | 11/2012 | Siejko et al. |
| 8,371,686 B2 | 2/2013 | Ghanem et al. |
| 8,380,294 B2 | 2/2013 | Messier et al. |
| 8,626,279 B2 | 1/2014 | Edvardsen et al. |
| 8,652,048 B2 | 2/2014 | Skerl et al. |
| 8,688,469 B2 | 4/2014 | Ziegler et al. |
| 9,022,945 B2 | 5/2015 | Fayram et al. |
| 9,144,384 B2 | 9/2015 | Margarida et al. |
| 9,420,956 B2 | 8/2016 | Gopalakrishnan et al. |
| 9,622,664 B2 | 4/2017 | An et al. |
| 9,629,548 B2 | 4/2017 | Sachanandani et al. |
| 9,993,165 B2 | 6/2018 | Thakur et al. |
| 10,182,768 B2 | 1/2019 | Zhang et al. |
| 10,271,797 B2 | 4/2019 | Zhang et al. |
| 10,278,653 B2 | 5/2019 | Averina et al. |
| 10,528,848 B2 | 1/2020 | Madabhushi et al. |
| 10,555,704 B2 | 2/2020 | Averina et al. |
| 10,595,775 B2 | 3/2020 | Soykan |
| 10,660,536 B2 | 5/2020 | Wang et al. |
| 10,991,463 B2 | 4/2021 | Kutzko et al. |
| 11,083,371 B1 | 8/2021 | Szabados et al. |
| 11,139,082 B2 | 10/2021 | Grodzki et al. |
| 11,166,679 B2 | 11/2021 | Bhat et al. |
| 11,177,024 B2 | 11/2021 | Cheng et al. |
| 11,177,041 B1 | 11/2021 | Sutton et al. |
| 11,195,616 B1 | 12/2021 | Seemakurty et al. |
| 11,207,033 B2 | 12/2021 | Aarts |
| 11,246,541 B1 | 2/2022 | McNair |
| 11,253,185 B2 | 2/2022 | Szabados et al. |
| 11,253,186 B2 | 2/2022 | Szabados et al. |
| 11,276,495 B2 | 3/2022 | Wallis et al. |
| 11,298,069 B2 | 4/2022 | Chauhan et al. |
| 11,350,888 B2 | 6/2022 | Krebs et al. |
| 11,375,941 B2 | 7/2022 | Szabados et al. |
| 11,501,862 B2 | 11/2022 | Nida et al. |
| 11,515,039 B2 | 11/2022 | Kolatkar et al. |
| 11,583,687 B2 | 2/2023 | Dani et al. |
| 11,587,678 B2 | 2/2023 | Goetz et al. |
| 11,610,686 B1 | 3/2023 | Naghavi |
| 11,657,921 B2 | 5/2023 | Zimmerman et al. |
| 11,751,816 B1 | 9/2023 | McNair |
| 11,864,944 B2 | 1/2024 | Fornwalt et al. |
| 11,869,668 B2 | 1/2024 | Nemani et al. |
| 11,890,116 B2 | 2/2024 | Thakur et al. |
| 2016/0135706 A1 | 5/2016 | Sullivan et al. |
| 2019/0108912 A1 | 4/2019 | Spurlock, III et al. |
| 2019/0110756 A1 | 4/2019 | Sharma et al. |
| 2020/0108260 A1 | 4/2020 | Haddad et al. |
| 2020/0178903 A1 | 6/2020 | Chaudhuri et al. |
| 2020/0187865 A1 | 6/2020 | Sharma et al. |
| 2020/0297230 A1* | 9/2020 | Thakur ............... A61B 5/0205 |
| 2020/0357517 A1 | 11/2020 | Haddad et al. |
| 2020/0357518 A1 | 11/2020 | Musgrove et al. |
| 2021/0020294 A1 | 1/2021 | Bharmi et al. |
| 2021/0093254 A1 | 4/2021 | Sarkar et al. |
| 2021/0183525 A1 | 6/2021 | Overhage et al. |
| 2021/0186368 A1 | 6/2021 | Kawecki et al. |
| 2021/0307700 A1 | 10/2021 | Brue et al. |
| 2021/0315473 A1 | 10/2021 | Chan et al. |
| 2021/0338174 A1 | 11/2021 | Weffers-Albu et al. |
| 2021/0345934 A1 | 11/2021 | Landgraf et al. |
| 2021/0382472 A1 | 12/2021 | Roy et al. |
| 2021/0391079 A1 | 12/2021 | Clifton et al. |
| 2022/0039729 A1 | 2/2022 | Fontanarava et al. |
| 2022/0059238 A1 | 2/2022 | Hame et al. |
| 2022/0092771 A1 | 3/2022 | Itu et al. |
| 2022/0096020 A1 | 3/2022 | Ahmed et al. |
| 2022/0175299 A1 | 6/2022 | Jadidi et al. |
| 2022/0203364 A1 | 6/2022 | An et al. |
| 2022/0218225 A1 | 6/2022 | Suda et al. |
| 2022/0240845 A1 | 8/2022 | Holmes et al. |
| 2022/0273236 A1 | 9/2022 | Zhou |
| 2022/0304612 A1 | 9/2022 | Davis et al. |
| 2022/0336088 A1 | 10/2022 | Thomas et al. |
| 2022/0369961 A1 | 11/2022 | Mothilal et al. |
| 2023/0026404 A1 | 1/2023 | Moore |
| 2023/0040463 A1 | 2/2023 | Sjolin et al. |
| 2023/0102301 A1 | 3/2023 | Nakatsugawa |
| 2023/0105385 A1 | 4/2023 | Ganesan et al. |
| 2023/0107589 A1 | 4/2023 | Buda et al. |
| 2023/0153605 A1 | 5/2023 | Tang |
| 2023/0187041 A1 | 6/2023 | Teterin |
| 2023/0238134 A1 | 7/2023 | Ravishankar et al. |
| 2023/0245782 A1 | 8/2023 | Zimmerman et al. |
| 2023/0301601 A1 | 9/2023 | Averina et al. |
| 2023/0346288 A1 | 11/2023 | Hughes et al. |
| 2023/0380773 A1 | 11/2023 | Burnes et al. |
| 2023/0395248 A1 | 12/2023 | Sipe et al. |
| 2023/0411018 A1 | 12/2023 | Lee et al. |
| 2024/0047067 A1 | 2/2024 | Bahl et al. |
| 2024/0047072 A1* | 2/2024 | Haddad ............... A61B 5/0006 |
| 2024/0186016 A1 | 6/2024 | Kesar |

FOREIGN PATENT DOCUMENTS

| | | |
|---|---|---|
| EP | 2091421 B1 | 4/2016 |
| EP | 3387569 A1 | 10/2018 |
| EP | 3054840 B1 | 8/2020 |
| EP | 3355985 B1 | 11/2020 |
| EP | 3250287 B1 | 8/2021 |
| EP | 3048953 B1 | 12/2021 |
| EP | 4033971 A1 | 8/2022 |
| EP | 4124285 A1 | 2/2023 |
| EP | 4145133 A1 | 3/2023 |
| EP | 4145467 A1 | 3/2023 |
| EP | 4160617 A1 | 4/2023 |
| EP | 4192354 A1 | 6/2023 |
| WO | 2021148967 A1 | 7/2021 |
| WO | 2022173674 A1 | 8/2022 |
| WO | 2022245804 A1 | 11/2022 |
| WO | 2023088767 A1 | 5/2023 |
| WO | 2023094455 A1 | 6/2023 |
| WO | 2023102161 A1 | 6/2023 |
| WO | 2023223209 A1 | 11/2023 |
| WO | 2024010616 A1 | 1/2024 |
| WO | 2024035530 A1 | 2/2024 |
| WO | 2024110802 A1 | 5/2024 |
| WO | 2024123547 A1 | 6/2024 |

* cited by examiner

METHODS AND SYSTEMS FOR PREDICTING ARRHYTHMIA RISK UTILIZING MACHINE LEARNING MODELS

RELATED APPLICATION

The present application claims priority to U.S. Provisional Application No. 63/167,213, Titled "METHODS AND SYSTEMS FOR PREDICTING ARRHYTHMIA RISK UTILIZING MACHINE LEARNING MODELS" which was filed on 29 Mar. 2021, the complete subject matter of which is expressly incorporated herein by reference in their entirety.

FIELD OF THE INVENTION

Embodiments herein relate generally to predicting arrhythmia risk based on cardiac activity signals utilizing machine learning models.

BACKGROUND OF THE INVENTION

Today, patients with various indications receive different types of implantable medical devices (IMDs). One type of IMD is an implantable cardiac monitor (ICM) that is implanted in a pectoral pocket and monitors cardiac activity without the ability to deliver a therapy. Other types of IMDs are configured to deliver a therapy, such as a pacemaker, implantable cardioverter defibrillator (ICD), cardiac rhythm management (CRM) device, leadless device, subcutaneous device and the like.

Numerous arrhythmia detection processes are implemented within IMDs to detect arrhythmias based on various criteria, such as rates, irregularities and variation patterns in R-wave to R-wave (RR) intervals. In some embodiments, the arrhythmia detection process steps beat by beat through cardiac activity (CA) signals and analyzes the characteristics of interest, such as RR rate, RR interval, RR patterns and the like. An arrhythmia episode is declared based on the characteristics of interest.

ICDs are commonly implanted in patients who meet certain clinical criteria such as prior cardiac arrest or structural heart disease. However, some patients, who do not meet the implant criteria, may still suffer a ventricular arrhythmia. Without an ICD these patients may not receive life-saving treatment in time. To predict whether a patient with no prior indication might need an ICD, an ICM system may be used. ICMs are much less expensive than ICDs and have fewer associated clinical risks. An ICM may be configured to simply store CA strips of EGM signals for various periods of time, and/or monitor the CA signals for one or more characteristics of interest (COI) and declares an arrhythmia when the COI is present. When the ICM detects and identifies a certain number, type or severity of prior arrhythmias, such determination may be treated as an indication that the patient should receive an IMD capable of delivering therapy.

However, existing ICMs and other types of IMDs (as well as existing supporting external devices or medical network servers) do not have the ability to "predict" the potential that an arrhythmia episode is likely to occur in the future based on normal/physiologic EGM signals.

A need remains to provide a manner to calculate a risk factor that a future arrhythmia is likely to occur before the arrhythmia episode occurs.

SUMMARY

In accordance with embodiments herein, a system for determining an arrhythmia risk is provided. The system includes memory to store specific executable instructions and a machine learning (ML) model trained to predict an arrhythmia with a characteristic of interest (COI) that exhibits a non-physiologic behavior. One or more processors are configured to execute the specific executable instructions to obtain CA signals collected by an implantable medical device (IMD), wherein the COI exhibits a physiologic behavior and apply the ML model to the CA signals to identify a risk factor that a patient will experience the arrhythmia at a future point in time even though the COI in the CA signals, exhibits a physiologic behavior.

Optionally, they system may comprise an IMD. The IMD may include at least one processor from the one or more processors configured to apply an arrhythmia detection algorithm to analyze the CA signals over a series of beats to determine whether the COI exhibits a physiologic or non-physiologic behavior. The arrhythmia detection algorithm may determine that the CA signals are not indicative of the arrhythmia, while the ML model may determine that the CA signals indicate the risk factor to indicate a first risk level that the patient will experience the arrhythmia within the future predetermined period of time.

Optionally, the risk factor may be indicative of at least one of: i) a scale ranging from low to high risk levels, ii) a time prediction indicating a period of time until the patient is likely to have the arrhythmia, iii) an arrhythmia severity, or iv) a confidence probability regarding accuracy of the risk factor. They system may comprise a display configured to present an alert regarding the risk factor. The ML model may represents a convolutional neural network comprising sub-layers and including one or more convolutional layers, activation functions, and/or normalization.

Optionally, they system may comprise an IMD. The IMD may include a combination of subcutaneous electrodes configured to collect the CA signals. The IMD, may include IMD memory configured to store program instructions and one or more IMD processors configured to execute the program instructions to analyze the CA signals and based on the analysis declare arrhythmias episodes and a transceiver configured to wirelessly transmit the CA signals to an external device.

Optionally, the system may include a server that includes the memory and the one or more processors. The memory may be configured to store the CA signals and to apply the ML model to the CA signals to identify the risk factor. The ML model may include a pseudo SG model configured to utilize machine learning to generate pseudo CA signals based on actual CA signals. The pseudo CA signals may be associated with a pseudo sensing vector. The actual CA signals may be collected by a second IMD along an actual sensing vector.

Optionally, thee one or more processors may be configured to train the pseudo CA signal model by obtaining, for a reference collection of beats, both of first and second collections of CA signals collected along first and second sensing vectors utilizing first and second combinations of sensing electrodes, respectively and training the pseudo CA signal model to convert the first collection of CA signals to a corresponding collection of pseudo CA signals associated with the second sensing vector and second combination of sensing electrodes.

Optionally, the first combination of sensing electrodes and first sensing vector may correspond to a transvenous configuration, while the second combination of sensing electrodes and second sensing vector may correspond to a non-transvenous subcutaneous configuration. The pseudo CA signals may be artificially generated by the pseudo CA signal generator to simulate a morphology of CA signals collected in connection with a non-transvenous subcutaneous configuration. The future point in time may begin at a point in time after the CA signals are collected by the IMD.

Optionally, the CA signals may represent subcutaneous electrocardiogram (EGM) signals for a series of beats over a predetermined period of time, the COI corresponding to at least one of: i) R-R rate, ii) R-R interval variability, iii) P-P rate, iv) P-P interval variability iv) a P-wave occurrence, v) an R-wave occurrence, vi) ST segment level, vii) ST segment variability, or viii) the PQRST complex, the COI of the EGM signals exhibiting a physiologic behavior.

In accordance with embodiments herein, a computer implemented method is provided. The method is under control of one or more processors configured with specific executable instructions. The method provides a machine learning (ML) model trained to predict an arrhythmia with a characteristic of interest (COI) that exhibits a non-physiologic behavior and obtains CA signals collected by an implantable medical device (IMD), wherein the COI in the CA signals, exhibits a physiologic behavior. The method applies the ML model to the CA signals to identify a risk factor that a patient will experience the arrhythmia at a future point in time even though the COI from the CA signals, exhibits a physiologic behavior.

Optionally, the method may apply an arrhythmia detection algorithm to analyze the CA signals over a series of beats to determine whether the COI exhibits a physiologic or non-physiologic behavior. The arrhythmia detection algorithm may determine that the CA signals are not indicative of the arrhythmia, while the ML model may determine that the CA signals indicate the risk factor to indicate a first risk level that the patient will experience the arrhythmia within the future predetermined period of time.

Optionally, the risk factor may be indicative of at least one of: i) a scale ranging from low to high risk levels, ii) a time prediction indicating a period of time until the patient is likely to have the arrhythmia, iii) an arrhythmia severity, or iv) a confidence probability regarding accuracy of the risk factor. The method may present an alert regarding the risk factor.

Optionally, the ML model may represent a convolutional neural network comprising sub-layers and including one or more convolutional layers, activation functions, and/or normalization. The ML model may include a pseudo SG model configured to utilize machine learning to generate pseudo signals based on actual CA signals. The pseudo CA signals may be associated with a pseudo sensing vector. The actual CA signals may be collected by a second IMD along an actual sensing vector. The ML model may include an arrhythmia prediction model configured to utilize machine learning to generate the risk factor based on the CA signals.

Optionally, the first combination of sensing electrodes and first sensing vector may correspond to a transvenous configuration, while the second combination of sensing electrodes and second sensing vector may correspond to a non-transvenous subcutaneous configuration. The pseudo CA signals may be artificially generated by the pseudo CA signal generator to simulate a morphology of CA signals collected in connection with a non-transvenous subcutaneous configuration.

Optionally, the ML model may include an arrhythmia risk prediction model configured to utilize machine learning trained to predict, as the risk factor. The risk may be that the patient will experience a ventricular arrhythmia. The risk factor may indicate a likelihood that the patient will experience the arrhythmia within a three month time period following a time when the CA signals are collected by the IMD.

DETAILED DESCRIPTION

Figure 1:
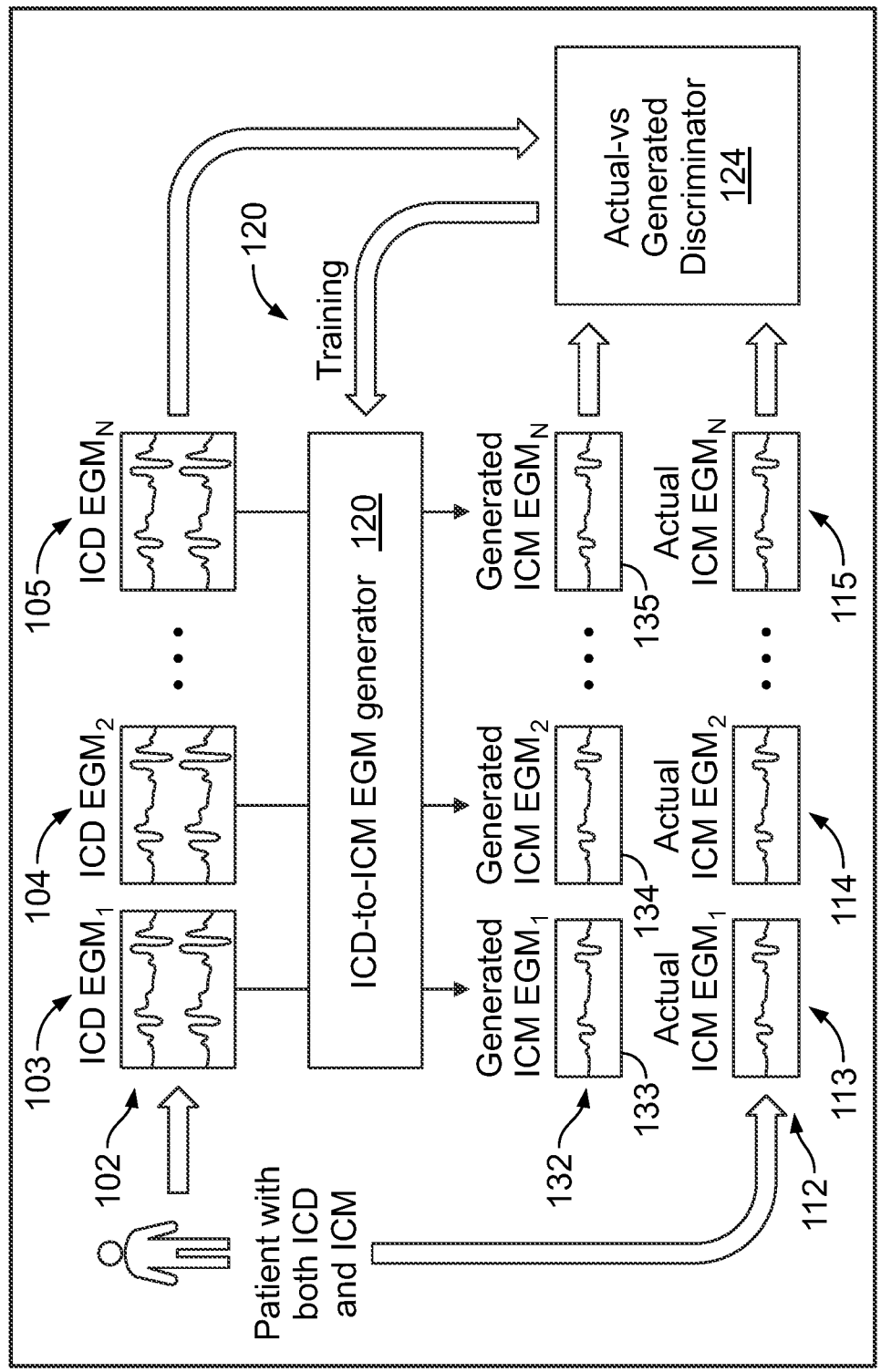
FIG. 1 illustrates a machine learning process to train a model to convert actual CA signals into pseudo CA signals in accordance with embodiments herein.

The terms "cardiac activity signal", "cardiac activity signals", "CA signal" and "CA signals" (collectively "CA signals") are used interchangeably throughout and shall mean an analog or digital electrical signal recorded by two or more electrodes positioned transvenous, subcutaneous or cutaneous, where the electrical signals are indicative of cardiac electrical activity. The cardiac activity may be normal/physiologic or abnormal/non-physiologic/arrhythmic. Non-limiting examples of CA signals include ECG signals collected by cutaneous electrodes, and EGM signals collected by transvenous electrodes and/or non-transvenous, subcutaneous electrodes.

The term "active sensing vector" shall refer to a path extending between two or more physical, actual electrodes that operate as sensing sites.

The term "COI" refers to a characteristic of interest that, as nonlimiting examples, may include at least one of: i) R-R rate, ii) R-R interval variability, iii) P-P rate, iv) P-P interval variability iv) a P-wave occurrence, v) an R-wave occurrence, vi) ST segment level, or vii) ST segment variability. A COI may relate to one or more components of the PQRST complex, but does not necessarily relate to multiple or all of the components of the PQRST complex.

The term "PQRST complex" shall refer to corresponding P, Q, R, S, and T components of CA signals, such as in ECG or EGM signals.

The term "pseudo sensing vector" shall refer to a path extending to or from one or more pseudo sensing sites. A pseudo sensing site may or may not have a physical electrode at the corresponding site, but does not have an active sensing electrode (e.g., if an electrode is at the location it is not used in connection with sensing). Pseudo sensing vectors and pseudo sensing sites represent virtual or artificial vectors and sites associated with artificially generated pseudo signals.

The terms "pseudo cardiac activity signal", "pseudo cardiac activity signals", "pseudo CA signal", "pseudo CA signals", and "pseudo signals" (collectively "pseudo signals") are used interchangeably throughout and shall refer to cardiac activity signals that are not directly measured, but instead are automatically computer generated by one or more machine learning models based on actual cardiac activity signals. The actual CA signals are measured along a corresponding active sensing vector by an actual, active electrode combination as described throughout the present specification. The pseudo signals have a morphology that is identical or substantially similar to a morphology of CA signals if measured along the pseudo sensing vector between corresponding pseudo sensing sites. The pseudo signals are generated by the ML model to have a morphology that substantially correspond to a morphology of an actual CA signal, if such actual CA signal were measured between the corresponding pseudo sensing sites and along the corresponding sensing vector.

The term "subcutaneous" shall mean below the skin surface but not within the heart and not transvenous.

The term "device documented marker" refers to markers that are generated by an IMD to characterize one or more characteristics of interest within respective CA signals. Markers may be declared based on numerous criteria, such as signal processing, characteristic detection and arrhythmia detection software and hardware within and/or operating on the implantable cardiac monitor and/or implantable medical device.

The term "marker" shall mean data and/or information identified from CA signals that may be presented as graphical and/or numeric indicia indicative of one or more characteristics within the CA signals and/or indicative of one or more episodes exhibited by the cardiac events. Markers may be superimposed upon CA signals or presented proximate to, and temporally aligned with, CA signals. Non-limiting examples of markers may include R-wave markers, noise markers, activity markers, interval markers, refractory markers, P-wave markers, T-wave markers, PVC markers, sinus rhythm markers, AF markers and other arrhythmia markers. As a further nonlimiting example, basic event markers may include "AF entry" to indicate a beginning of an AF event, "in AF" to indicate that AF is ongoing, "AF exit" to indicate that AF has terminated, "T" to indicate a tachycardia beat, "B" to indicate a bradycardia beat, "A" to indicate an asystole beat, "VS" to indicate a regular sinus beat, "Tachy" to indicate a tachycardia episode, "Brady" to indicate a Bradycardia episode, "Asystole" to indicate an asystole episode, "Patient activated" to indicate a patient activated episode. An activity marker may indicate activity detected by activity sensor during the CA signal. Noise markers may indicate entry/start, ongoing, recovery and exit/stop of noise. Markers may be presented as symbols, dashed lines, numeric values, thickened portions of a waveform, and the like. Markers may represent events, intervals, refractory periods, ICM activity, and other algorithm related activity. For example, interval markers, such as the R-R interval, may include a numeric value indicating the duration of the interval. The AF markers indicate atrial fibrillation rhythmic.

The terms "beat" and "cardiac event" are used interchangeably and shall include both normal or abnormal events.

The terms "normal", "physiologic" and "sinus" are used to refer to events, features, and characteristics of, or appropriate to, a heart's healthy or normal functioning.

The terms "abnormal," "non-physiologic" and "arrhythmic" are used to refer to events, features, and characteristics of, or appropriate to, an un-healthy or abnormal functioning of the heart.

The term "EDT" shall mean an external diagnostic test.

The term "machine learning" shall mean an artificial intelligence algorithm that learns from various automatic or manual inputs, such as features of interest, prior device classified arrhythmias, observations and/or data. The machine learning algorithm is adjusted over multiple iterations based on the features of interest, prior device classified arrhythmias, observations and/or data. For example, the machine learning algorithm is adjusted by supervised learning, unsupervised learning, and/or reinforcement learning. Non-limiting examples of machine learning algorithms are a convolutional neural network, gradient boosting random forest, decision tree, K-means, deep learning, artificial neural network, and/or the like. The machine learning model may include a convolutional neural network architecture. It is recognized that the network architecture may differ and/or other types of machine learning models may be utilized. As non-limiting examples, the architecture may comprise of N network layers, each with M sub-layers followed by pooling and normalization. The architecture components may include: 1-dimensional convolutional layers ("Conv1D"), rectified linear unit ("relu") activation functions, batch normalization ("BN"), etc. The network output may be a continuous value between 0 and 1, where values close to zero indicate high confidence that the CA signals indicate a low risk that an arrhythmia is likely to occur, and values close to 1 indicate high confidence that the CA signals indicate a high risk that an arrhythmia is likely to occur.

The term "obtain", as used in connection with data, signals, information and the like, includes at least one of i) accessing memory of an IMD, ICM, external device or remote server where the data, signals, information, etc. are stored, ii) receiving the data, signals, information, etc. over a wireless communications link between the ICM or IMD and a local external device, iii) receiving the data, signals, information, etc. at a remote server over a network connection and/or iv) sensing signals (e.g., CA signals, impedance signals, etc.) between a combination of electrodes provide on or coupled to the ICM or IMD. An obtaining operation, when from the perspective of an ICM or IMD, may include sensing new signals in real time, and/or accessing memory to read stored data, signals, information, etc. from memory within the ICM or IMD. The obtaining operation, when from the perspective of a local external device, includes receiving the data, signals, information, etc. at a transceiver of the local external device where the data, signals, information, etc. are transmitted from an ICM and/or a remote server. The obtaining operation may be from the perspective of a remote server, such as when receiving the data, signals, information, etc. at a network interface from a local external device and/or directly from an ICM. The remote server may also obtain the data, signals, information, etc. from local memory and/or from other memory, such as within a cloud storage environment and/or from the memory of a workstation or clinician external programmer.

The terms "patient data entry device" and "PDE device" shall mean an electronic device that includes a user interface that is configured 1) to receive patient data that is entered by the patient and/or 2) to receive patient data in connection with actions/decisions by the patient. A PDE device is different from an IMD and a BGA test device. The PDE device is configured to receive behavior related medical data that differs from IMD data and that differs from BGA data. The PDE devices may include, but are not limited to, smart phones, desktop or laptop computers, tablet devices, smart TVs, fixed cameras, smart watch, wearable heart rate monitor, portable or handheld cameras, recording devices, digital personal assistant (DPA) devices and the like. One nonlimiting example of a PDE device is a smart phone implementing the "HEMAAPP" application, developed at the University of Washington, where the application is configured to utilize a camera within a smart phone to monitor a patient's hemoglobin level (while holding a finger over the camera) and to detect when the patient is in an anemic or other undesirable state related to hemoglobin levels. Another example is a smart phone application developed by Wilbur Lam at the Aflac Cancer and Blood Disorders Center of Children's Healthcare of Atlanta, and Wallace Coulter, a faculty member in the Department of biomedical engineering at Georgia Tech. The PDE device may include an electronic device sold under the trademark ALEXA® by Amazon.com Inc., and/or an electronic device sold under the trademark NOW® by Google LLC., and the like. In addition, the PDE devices may represent various types of devices configured to record audio and/or voice signatures, detect gestures and movements and the like. The PDE device may include a graphical user interface, through which the patient or another user enters the patient data. Optionally, the PDE device may include audio and/or video sensors/cameras that may receive patient data. For example, a user may use a keyboard, touch screen and/or mouse to enter patient data. Optionally, the user may enter the patient data through spoken words (e.g., "Alexa I just took my medication", "Alexa I am eating 3 slices of peperoni pizza", "Alexa I am eating an apple", "Alexa I am drinking a 12 oz. soda and eating a candy bar). Optionally, the PDE device may automatically track actions by a patient, such as through the use of cameras to visually watch a patients actions, through the use of microphones to "listen" to a patient's actions, and/or through the use of other types of sensors (e.g., refrigerator or kitchen cabinet door sensor, sensor on a treadmill). For example, a camera may capture video that is processed by a processor utilizing image recognition to identify what a patient is eating/drinking, when the patient eats/drinks, and how much the patient consumed. Optionally, the BRM device may include a position tracking device sold under the trademark FITBIT® by Fitbit Inc. or other types of position tracking devices. The position tracking device may monitor and collect, as BRM data, movement information, such as a number of steps or distance traveled in a select period of time, a rate of speed, a level of exercise and the like. Optionally, the BRM device may monitor and collect, as BRM data, heart rate.

The term "probability" shall mean, not only a determined percentage or numerical value, but also non-numerical values and corresponding indicators. For example, a risk score algorithm may be used to determine a risk range or risk category a patient falls into with the range or risk category illustrated by color, bars, and the like. Such probability may also include morphological comparisons such as comparisons of waveforms in graphs associated with heart related data. In this manner, probability is simply the factoring or use of event related variable(s) to determine the likelihood an event will or won't occur. The probability thus may be represented in numerous manners, including a risk score, a subsequent risk score, a percentage, a bar graph, a range, a color-coded indicator, text indicia providing an indicator text such as "low", "medium", and "high", pictorially, and the like.

The term "real-time" shall refer to a time period substantially contemporaneous with an event of interest. The term "real-time," when used in connection with collecting and/or processing data utilizing an IMD, shall refer to processing operations performed substantially contemporaneous with a physiologic event of interest experienced by a patient. By way of example, in accordance with embodiments herein, cardiac activity signals are analyzed in real time (e.g., during a cardiac event or within a few minutes after the cardiac event). The term "real-time," when used in connection with a body generated analyte, shall refer to operations performed substantially contemporaneous with an occurrence of a characteristic of interest in a malnutrition state experienced by the patient. By way of example, in accordance with embodiments herein, the body generated analyte may correspond to serum albumin that is analyzed and utilized in a diagnosis and treatment recommendation. The analysis of the serum albumin and generation of the diagnosis and treatment recommendation are performed in real-time, namely while the patient is experiencing a certain malnutrition state, not to exceed 24 hours from the time the BGA was collected.

The term "treatment notification" shall mean a communication and/or device command to be conveyed to one or more individuals and/or one or more other electronic devices, including but not limited to, network servers, workstations, laptop computers, tablet devices, smart phones, IMDs, PDE equipment and the like. When a treatment notification is provided as a communication, the treatment notification may represent in an audio, video, vibratory or other user perceivable medium. The communication may be presented in various formats, such as to display patient information, messages, user directions and the like. The communication is presented on one or more of the various types of electronic devices described herein and may be directed to a patient, a physician, various medical personnel, various patient record management personnel and the like. The communication may represent an identification of a risk factor (e.g. patient diagnosis) and various treatment recommendations. The risk factor and treatment recommendation may be provided directly to the patient. For example, in some circumstances, a diagnosis and treatment recommendation may be to modify a dosage level, in which case, the notification may be provided to the physician or medical practitioner. As another example, the diagnosis and treatment recommendation may be to begin, change or end certain physical activities, in which case, the notification may be provided to the patient, in addition to the physician or medical practitioner. As another example, the treatment notification may present an indication that a patient may or may not be a good candidate suited for implant of a ventricular assist device (e.g., LV assist device), a transplant, a valve repair procedure (e.g., a MitraClip™ valve repair to correct mitral regurgitation) and the like. Other nonlimiting examples of a communication type notification include, in part or in whole, a recommendation to schedule an appointment with a physician, schedule an appointment for additional blood work, perform an additional at home blood analysis (e.g., utilizing at home equipment), recommend that the patient collect additional IMD data. When a notification includes an action that may be performed by a patient alone, the notification may be communicated directly to the patient. Other nonlimiting examples of a communication type notification include communications sent to a patient (e.g., via a PDE device or other electronic device), where the communication informs the patient of how a patient's lifestyle choices are directly affecting the patient's health. For example, when a patient consumes too much sugar, a notification may be sent to the patient to inform that the excessive sugar has caused a spike in the patient's glucose level. As another example, when a patient avoids exercise for a period of time, the notification may inform a patient that the patient's lack of exercise has raised a PAP trend and/or introduced an undue burden on a patient's kidneys.

When a treatment notification is provided as a device command, the treatment notification may represent an electronic command directing a computing device (e.g., IMD, EDT equipment, local external device, server) to perform an action. For example, the action may include directing the following:

1. IMD or EDT equipment to provide additional IMD data and/or EDT data already available;
2. IMD or EDT equipment to collect additional data and/or another type of data;
3. IMD to deliver a therapy and/or modify a prior therapy (e.g., a pacing therapy, neural stimulation therapy, appetite suppression therapy, drug delivery rate);
4. Local external device to provide additional information regarding past and present behavior of the patient; and
5. Server to analyze further information in the patient medical record and/or from another medical record.

The term "treatment recommendation" shall mean a recommendation for the patient, medical personnel and/or a device (e.g., an IMD, local external device, remote server, or BGA device) to take an action and/or maintain a current course of action. Non-limiting examples of treatment recommendations include dispatching an ambulance to the patient's location, instructing the patient immediately go to a hospital, instructing the patient schedule an appointment, instructing the patient change a prescription, instructing the patient undergo additional examinations (e.g., diagnostic imaging examinations, exploratory surgery and the like), instructing the patient undergo a POC test to collect new BGA data, instructing the patient take a nutritional supplement (e.g., an ONS), instructing the patient start, stop or change a physical activity, or instructing the patient make no changes. The treatment recommendation may include an instruction to change, maintain, add or stop a therapy delivered by an active IMD, such as a pacing therapy, and ATP pacing therapy, a neural stimulation therapy, mechanical circulatory support and the like.

FIG. 1 illustrates a machine learning process to train a model to convert actual CA signals into pseudo CA signals in accordance with embodiments herein. In accordance with methods and systems herein, the process simultaneously obtains both of first and second collections of CA signals for a reference collection of beats. The first and second collections of CA signals are collected along first and second sensing vectors utilizing first and second combinations of sensing electrodes, respectively. For example, the patient may have two implantable devices (e.g. an ICD and an ICM), each of which utilizes separate combinations of sensing electrodes that define corresponding separate sensing vectors. The first IMD (e.g. an ICD) collects the first collection of CA signals 102 which includes CA signal segments 103-105 for corresponding periods of time. For example, each segment 103-105 may correspond to 1-7 beats, a series of beats over 10-30 seconds, a series of beats over one minute, and the like. For the same period(s) of time, the second IMD (e.g. an ICM) collects the CA signal segments 113-115 to form the second collection of CA signals 112. The CA signal segments 103-15 and 113-115 represent actual CA signals collected along an actual sensing vector between active electrode combinations. The CA signal segments 103 and 113 are collected contemporaneously for the same series of beats. The CA signal segments 104 and 114 are collected contemporaneously for the same series of beats. The CA signal segments 105 and 115 are collected contemporaneously for the same series of beats.

The process then trains a machine learning (ML) model 120, also referred to as a pseudo signal generating (SG) model. The model 120 may represent a convolutional neural network comprising sub-layers and including one or more convolutional layers, activation functions, and/or normalization. The pseudo SG model 120 is trained to convert the first collection of actual CA signals 102 to a corresponding collection of pseudo signals 132. The pseudo SG model 120 includes a pseudo signal generator that, during training, communicates with an actual versus generated discriminator 124. The collection of pseudo signals 132 are artificially generated by the pseudo SG generator 120. The discriminator 124 compares the pseudo signals 132 to the second collection of actual CA signals 112. More specifically, the discriminator 124 compares each of the pseudo signal segments 133-135 to the corresponding CA signal segments 113, 115. The discriminator 124 provides training feedback to the pseudo SG model 120 which updates the machine learning model therein and generates a next version of the collection of pseudo signals 132. The process is iteratively repeated a large number of times while the pseudo SG model 120 is trained based on the feedback from the discriminator 124 until the pseudo signals 132 are substantially similar to or indistinguishable from the second collection of CA signals 112.

In the example of FIG. 1, the first combination of active sensing electrodes and first active sensing vector correspond to a transvenous configuration, while the second combination of active sensing electrodes and second active sensing vector correspond to a non-transvenous subcutaneous configuration. The pseudo signals are artificially generated by the pseudo SG model 120 to simulate a morphology of CA signals collected in connection with a non-transvenous subcutaneous configuration, that substantially resembles the morphology of the second collection of actual CA signals 112. For example, the transvenous configuration may include one or more transvenous leads within the RA, RV, or other chamber of the heart, while the IMD is located in a pectoral region. Additionally or alternatively, the transvenous configuration may represent one or more leadless pacemakers implanted entirely within one or more of the RA, RV or other chamber of the heart. The non-transvenous subcutaneous configuration may include one or more implantable cardiac monitors implanted entirely within a pectoral region without any lead extending therefrom. Additionally or alternatively, the non-transvenous subcutaneous configuration may include one or more subcutaneous leads, such as extending along the rib cage, along the sternum or elsewhere outside of the heart, while the IMD is located in a pectoral pocket, lateral anterior region and the like. Optionally, the CA signals represent subcutaneous electrocardiogram (EGM) signals for a series of beats over a predetermined period of time. The COI may correspond to at least one of: i) R-R rate, ii) R-R interval variability, iii) P-P rate, iv) P-P interval variability iv) a P-wave occurrence, v) an R-wave occurrence, vi) ST segment level, or vii) ST segment variability. The COI of the EGM signals exhibit a normal/physiologic behavior.

By way of example, the pseudo SG model 120 may implement a machine learning technique known as "Generative Adversarial Networks" (GANs). In a GAN, one "generator" is trained to convert the first collection of CA signals 102 while a separate "discriminator" 124 is trained to detect whether the output (pseudo signals 132) represent an "actual" or "generated/pseudo" output. The two networks (120 and 124) compete, and training continues until the discriminator 124 can no longer reliably detect the difference between actual and generated/pseudo CA signal. The GANs preserve all predictive signal features of the actual CA signals in the pseudo CA signals, even predictive signal features which may not be considered relevant by a clinician.

Figure 2:
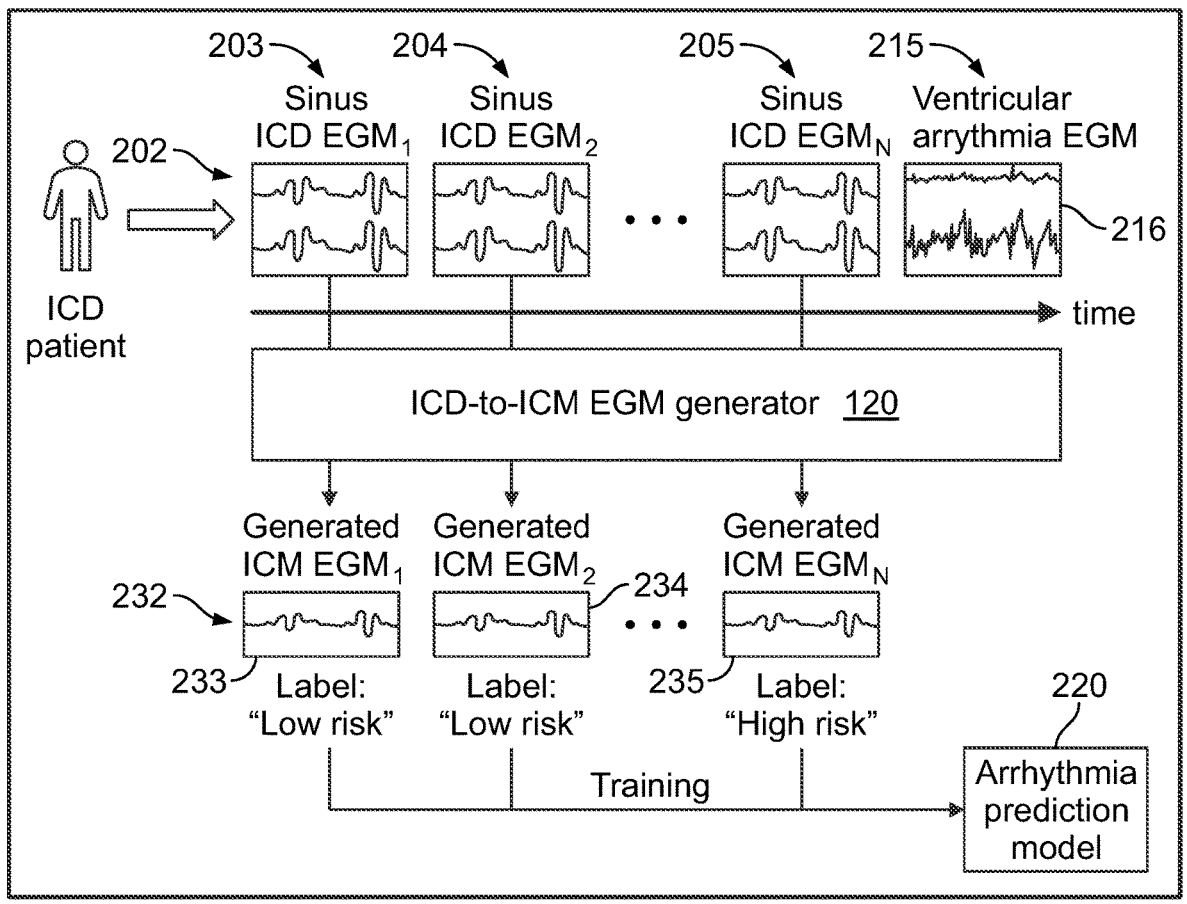
FIG. 2 shows a process for using the pseudo signal generating (SG) model (trained in connection with FIG. 1) to train a separate machine learning prediction model in accordance with embodiments herein.

FIG. 2 shows a process for using the pseudo SG model 120 (trained in connection with FIG. 1) to train a separate machine learning prediction model 220 in accordance with embodiments herein. In accordance with methods and systems herein, a new collection of CA signals 202 (separate from the collection used in FIG. 1) are provided as an input to the pseudo SG model 120. The collection of CA signals 202 precede a non-physiologic episode (e.g. an arrhythmia) experienced by the patient at a later point in time.

The new collection of CA signals 202 are collected by an IMD while the patient is experiencing a normal/physiologic condition. During the normal physiologic condition, the one or more characteristics of interest from the CA signals exhibit normal/physiologic behavior. The COI may be within the PQRST complex or elsewhere in the CA signals. For example, the collection of CA signals 202 may be collected along a transvenous sensing vector between i) one or more electrodes located in the RA and/or RV and ii) the CAN or housing of the IMD. As a further example, when an arrhythmia of interest represents ventricular fibrillation (VF) or ventricular tachycardia (VT), a COI may be the RR rate or RR interval variability, and the CA signals 202 are collected while the patient is experiencing normal/physiologic RR rates and RR interval variabilities. The collection of CA signals 202 includes a series of CA signal segments 203-205 that are collected over a period of time, such as separated over a series of days, weeks or longer. For example, CA signal segment 204 may be collected one or more weeks or months after collection of CA signal segment 203, while CA signal segment 205 is collected one or more weeks or months after collection of CA signal segment 204.

Optionally, the IMD includes one or more processors configured to apply an arrhythmia detection algorithm to analyze the CA signals over a series of beats to determine whether the COI exhibits a physiologic or non-physiologic behavior. The arrhythmia detection algorithm determines that the CA signals are not indicative of the arrhythmia, while the ML model determines that the CA signals indicate the risk factor to indicate a first risk level that the patient will experience the arrhythmia within the future predetermined period of time. Some period of time after collection of the CA signals 202, the patient experiences an arrhythmia episode which is detected by the IMD as denoted at 215. The physiologic CA signals are temporally tied/associated with the subsequent arrhythmia episode. During the arrhythmia, the IMD collects a corresponding arrhythmia signal segment 216 has a COI that exhibits a non-physiologic behavior. For example, the COI may exhibit an RR rate or RR interval variability that exceeds a corresponding threshold, thereby denoting VF or VT. As an example, the arrhythmia episode (and corresponding arrhythmia signal segment 216) may occur one or more hours, days or weeks after the collection of the recent CA signal segment 205. As a further example, the arrhythmia signal segment 216 may occur one or more days after the CA signal segment 205, one or more weeks after the CA signal segment 204 and multiple weeks or one or more months after the CA signal segment 203.

The pseudo SG model 120 converts the CA signals 202 (collected along the transvenous sensing vector) to pseudo signals 232 corresponding to a different pseudo sensing vector and pseudo electrode configuration. The conversion is based on the machine learning process developed by the pseudo SG model 120 during the training phase discussed in connection with FIG. 1. For example, the pseudo signals 232 may have a morphology that is identical or substantially similar to a morphology of actual CA signals collected by an ICM located in a pectoral region without any separate lead connected thereto. Additionally or alternatively, the pseudo signals 232 may have a morphology that is identical or substantially similar to a morphology of actual CA signals collected by a subcutaneous ICD.

A large number of collections of CA signal segment 202, that precede corresponding arrhythmia episodes 215, are provided to the pseudo SG model 120. The pseudo SG model 120 converts the collections of CA signals 202 into corresponding collections of pseudo signals 232. The collections of CA signals 202 and corresponding collections of pseudo signals 232 do not exhibit and are not collected during an arrhythmia episode, such as VF or VT, but are followed within a known period of time by an arrhythmia episode. For example, tens, hundreds or more collections of CA signal segments 202 (preceding corresponding known arrhythmia episodes) may be fed to the pseudo SG model 122 produce corresponding tens, hundreds or more collections of pseudo signals 232. The collections of pseudo signals 232 and the corresponding arrhythmia episodes, including the timing of the arrhythmia episodes, are fed to an arrhythmia prediction model 220.

Optionally, a risk factor is provided to the arrhythmia prediction model 220 in connection with each corresponding pseudo signal segment. The risk factor is indicative of a likelihood or probability that the patient will experience the arrhythmia episode at a future point in time even though the current corresponding pseudo signal segment exhibits normal/physiologic behavior (e.g a normal RR rate, normal RR interval variability). With reference to the example of FIG. 2, a pseudo signal segment 233 corresponds to a point in time several days, weeks or even months before a subsequent arrhythmia episode and thus is assigned a first or "low risk" factor. A later pseudo signal segment 234 also occurs a relatively large period of time before the arrhythmia episode and is similarly assigned the first or low risk factor. The pseudo signal segment 235 corresponds to a point in time immediately or shortly before the arrhythmia episode (e.g. a few days before, a few hours before) and is assigned a second or high risk factor.

Additionally or alternatively, the arrhythmia prediction model 220 may be provided with a risk factor indicative of at least one of: i) a scale ranging from low to high risk levels, ii) a time prediction indicating a period of time until the patient is likely to have the arrhythmia, iii) an arrhythmia severity, or iv) a confidence probability regarding accuracy of the risk factor.

The arrhythmia prediction model 220 is configured to utilize machine learning trained to predict, as the risk factor, the risk that the patient will experience a ventricular arrhythmia. For example, the risk factor indicates a likelihood that the patient will experience the arrhythmia within a three month time period following a point in time when the CA signals were collected by the IMD. The future point in time begins at a point in time after the CA signals are collected by the IMD.

Additionally or alternatively, the arrhythmia prediction model 220 may be trained based on actual CA signals and corresponding risk factors assigned by a clinician. For example, the pseudo signals 232 may represent pseudo EGM signals collected by an ICM (along a virtual sensing vector). The pseudo EGM signals may be supplemented with actual EGM signals collected by actual ICMs from a real patient population. The actual EGMs may be annotated with risk factors by a clinician. The actual EGMs and clinician denoted risk factors may then be provided to the arrhythmia prediction model 220.

Optionally, the arrhythmia prediction model 220 may be trained without provision of risk factors from a clinician. For example, the pseudo signals 232 may be provided to the arrhythmia prediction model, along with timestamps for when each pseudo signal segment 233-235 was recorded. The arrhythmia prediction model 220 may further be provided with a timestamp corresponding to the point in time when the arrhythmia episode occurred. The arrhythmia prediction model 220 may develop the risk factors based on the combination of the pseudo signal segments 233-235, timestamps associated with the pseudo signal segments 233-235, and the timestamp for when the arrhythmia episode occurred.

Additionally or alternatively, the arrhythmia prediction model 220 may receive a pseudo signal segment associated with the arrhythmia episode. For example, the EGM signal segment 216 (e.g. from a subcutaneous patch or transvenous lead system) may be converted to an arrhythmia pseudo signal that is provided to the arrhythmia prediction model 220. The arrhythmia prediction model 220 may develop the risk factors based on the combination of the pseudo signal segments 233-235 and the arrhythmia pseudo signal segment.

By building the machine learning models from the processes of FIGS. 1 and 2, embodiments herein enable an arrhythmia prediction model to be constructed for a type of IMD, electric configuration and/or sensing vector, for which a relatively small amount of prior direct patient information is available. For example, although transvenous ICDs have been in existence for several years and a large amount of data exist in connection there with preceding arrhythmia episodes, subcutaneous ICDs, ICMs and other types of IMDs are somewhat newer and do not have the same volume of historic patient population information. Embodiments herein are able to leverage patient data collected from various types of IMDs to be used to calculate risk factors for any given patient who has received an ICM, subcutaneous ICD or other newer type of IMD.

Additionally or alternatively, reference collections of CA signals may be utilized where some CA signal segments are known to include an arrhythmia of interest and other CA signal segments are known to not include an arrhythmia of interest. For example, a 30 second EGM strip may be utilized as one reference CA signal segment where the 30 second EGM strip is known to include an arrhythmia of interest. Multiple separate 30 second EGM strips are collected at different points in time for one patient, for a patient population, recorded by a variety of device types, device placements, device orientations and the like. where each of the separate 30 second EGM strips have CA signals that are known to include corresponding arrhythmias of interest. As a further example, a second collection of 30 second EGM strips are obtained where the second collection includes reference CA signal segments sets that are known to correspond to corresponding normal rhythms. The collection of reference CA signals may be recorded for one patient, a patient population, recorded by a variety of device types, device placements, device orientations and the like.

Optionally, the CA signals may be combined with device documented markers (e.g., R-wave markers, P-wave markers, RR intervals, AF designators) that identify the cardiac beats sensed by the device within the series of cardiac events. The cardiac activity data may have been previously acquired and stored in memory of an implantable or external monitoring device, implantable or external therapy delivery device, programmer, workstation, healthcare network or other system.

The CA signals are for one or more cardiac events spanning over various periods of time. As one example, multiple segments or sets of the cardiac activity data may be collected, where each segment/set is for an interval that is 30 seconds to 5 minutes in length. Optionally, the segments may include one or more IMD declared arrhythmia episodes. As another example, each of the segments or sets of the cardiac activity data may be collected for an interval that begins 10-60 seconds before an episode of interest (e.g., an AF episode) and that ends 10-60 seconds after the episode of interest. The CA signals may include one or multiple arrhythmia episodes.

Figure 3:
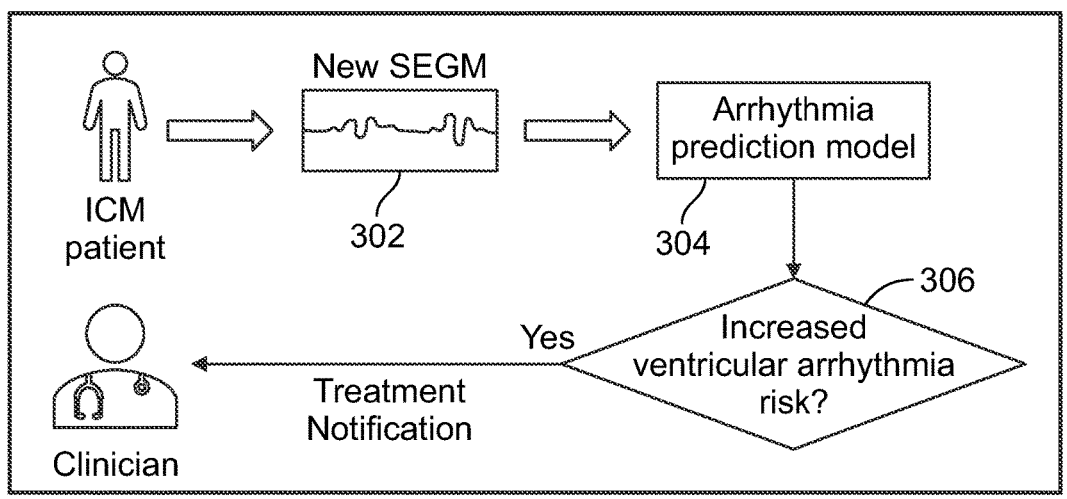
FIG. 3 illustrates a process for determining an arrhythmia risk in accordance with embodiments herein.

FIG. 3 illustrates a process for determining an arrhythmia risk. The process utilizes a risk prediction ML model trained to predict an arrhythmia with a COI that exhibits a non-physiologic behavior. The process of FIG. 3 may be implemented partially or entirely by one or more processors of an IMD. Optionally, an initial portion of the process of FIG. 3 may be implemented by the IMD, while the remaining operations are performed by a local external device and/or remote server.

At 302, one or more processors are configured to obtain CA signals collected by an IMD. The COI exhibits a physiologic behavior. The operation at 302 may be performed in real time, such as while an IMD is sensing actual CA signals along an active sensing vector between actual electrodes that operate as sensing sites. For example, the IMD may represent an ICM that comprises a combination of subcutaneous electrodes configured to collect the CA signals. The IMD includes IMD memory configured to store program instructions, and one or more IMD processors configured to execute the program instructions to: analyze the CA signals and based on the analysis declare arrhythmias episodes. The IMD further comprises a transceiver configured to wirelessly transmit the CA signals to an external device.

Additionally, the IMD may configure the one or more processors to apply an arrhythmia detection algorithm to analyze the CA signals over a series of beats to determine whether the COI (e.g., before, within or after the PQRST complex) exhibits a physiologic or non-physiologic behavior. The arrhythmia detection algorithm determines when the CA signals are indicative or are not indicative of the arrhythmia. The arrhythmia prediction models described herein determine the risk factor even though the arrhythmia detection algorithm may determine that the same CA signal segment indicates normal/physiologic behavior.

The operation at 302 may correspond to one or more CA signal segments. The ICM may be configured to wirelessly transmit CA signals to an external device. For example, the ICM may collect CA signal segments over a one-day interval of time, one or more weeks, one or more months and the like. Periodically, the ICM may transmit the CA signals to an external device. The frequency with which collections of CA signals are transmitted from the ICM to the external device and/or a remote server may be varied, such as based on risk factors identified from prior predictions. For example, over the course of a year, a patient may be determined to have a low risk of an arrhythmia episode, in which case, the ICM need only transmit the CA signals once each month or with some other relatively long interval between transmissions. In the event the patient's risk factor is increased to a medium or high risk factor, the process may direct the ICM to transmit CA signals more frequently, such as weekly and/or daily. In the event the risk factor is increased with patient, the process may further direct the ICM to collect CA signal segments more frequently, such as changing from once daily to four times a day, changing from four times a day to once each hour and the like.

The external device may be configured to locally process the one or more CA signal segments in accordance with embodiments herein. Additionally or alternatively, the external device may convey the one or more CA signal segments to a remote server which then performs the processing described herein to identify risk factors.

At 304, one or more processors apply the arrhythmia prediction model to the CA signals to identify a risk factor that a patient will experience the arrhythmia at a future point in time even though the COI exhibits a normal/physiologic behavior. The risk factor is indicative of at least one of: i) a scale ranging from low to high risk levels, ii) a time prediction indicating a period of time until the patient is likely to have the arrhythmia, iii) an arrhythmia severity, or iv) a confidence probability regarding accuracy of the risk factor. As explained herein, the arrhythmia prediction model is trained based on prior CA signals from the same type of IMD used to collect the CA signals at 302. For example, when the IMD at 302 represents an ICM, the training CA signals collected along active or pseudo-sensing vectors associated with an active electrode combination and/or a pseudo-electrode combination also correspond to an ICM. As another example, when the IMD at 302 represents a subcutaneous ICD, the training CA signals collected along active or pseudo-sensing vectors associated with an active electrode combination and/or a pseudo-electrode combination also correspond to a subcutaneous ICD.

The risk factor may be presented in various manners for example, the risk factor is indicative of at least one of: i) a scale ranging from low to high risk levels, ii) a time prediction indicating a period of time until the patient is likely to have the arrhythmia, iii) an arrhythmia severity, or iv) a confidence probability regarding accuracy of the risk factor. The risk factor may indicate a likelihood that the patient will experience the arrhythmia within a three month time period following a time when the CA signals are collected by the IMD. The future point in time begins at a point in time after the CA signals are collected by the IMD. As one example, the arrhythmia prediction is configured to utilize machine learning trained to predict, as the risk factor, the risk that the patient will experience a ventricular arrhythmia. As another example, the CA signals represent subcutaneous EGM signals for a series of beats over a predetermined period of time, while the COI corresponds to at least one of: i) R-R rate, ii) R-R interval variability, iii) P-P rate, iv) P-P interval variability iv) a P-wave occurrence, v) an R-wave occurrence, vi) ST segment level, or vii) ST segment variability, the COI of the EGM signals exhibiting a physiologic behavior.

At 306, the one or more processors determine whether the risk factor satisfies certain criteria, such as exceeding a threshold, increasing in risk and the like. For example, when the episode of interest represents a ventricular arrhythmia, the one or more processors may determine at 306 whether the risk of ventricular arrhythmia has exceeded a minimum threshold. When the risk factor exceeds the corresponding criteria, various actions may be taken, such as conveying a treatment notification to a clinician.

For example, the treatment notification may involve directing a display to present various types of alerts to a clinician regarding the risk factor. For example, the treatment notification may simply represent simply represent a status update to inform a clinician that a patient's risk factor still remains low. Alternatively, the treatment notification may include an alert that is generated and pushed to a clinician, such as to the clinician's phone, tablet device, various electronic communications accounts and the like. The treatment notification may inform the clinician that a patient status has changed from a low to medium risk, or from a medium to a high risk. Additionally or alternatively, the treatment notification may be sent to the patient. For example, the process of FIG. 3 may include an IMD wirelessly transmitting collections of CA signals to a home monitoring device. The home monitoring device may implement the arrhythmia prediction model and/or pass the collection of CA signals to a remote server that implements the arrhythmia prediction model. When the home monitor or server determined that the patient has entered a condition with a high risk that an arrhythmia episode is impending, a treatment notification may be pushed to the patient, such as to the patient's smart phone, tablet device, laptop computer or other electronic device. The treatment notification may inform the patient to schedule a visit with his/her clinician, go immediately to the hospital, take prescribed medication and/or perform some other action.

As a nonlimiting example, the treatment notification may indicate that an X probability exists that a patient will experience a VF or VT episode within Y days/weeks. Additionally or alternatively, the treatment notification may indicate that the arrhythmia episode has an X probability of being severe, or a wide probability of being moderate. Additionally or alternatively, the treatment notification may distinguish between potential types of arrhythmia episodes. For example, the clinician may be informed that a patient is likely to experience an arrhythmia episode having a minimal severity within the next several months, and/or the patient is likely to experience VF one or more times over the next three months, and/or the patient is likely to experience VT in the next week or more.

Optionally, the processes of FIGS. 1-3 may be implemented in connection with a holistic integrated healthcare patient management system, such as described in application Ser. No. 16/930,791, filed Jul. 16, 2020 and titled "METHODS, DEVICES AND SYSTEMS FOR HOLISTIC INTEGRATED HEALTHCARE PATIENT MANAGEMENT," incorporated herein by reference in its entirety. For example, the treatment notification may further request the patient to perform an additional test and/or collect additional information from one or more of the data collection sources described in the '791 application. For example, the treatment notification may request the patient to use a PDE device to enter certain information. Additionally or alternatively, the treatment notification may include the server or other external device automatically pulling previously acquired data captured by a PDE device and/or continuously acquiring and analyzing new data acquired by a PDE device, as described in the '791 application.

Figure 4:
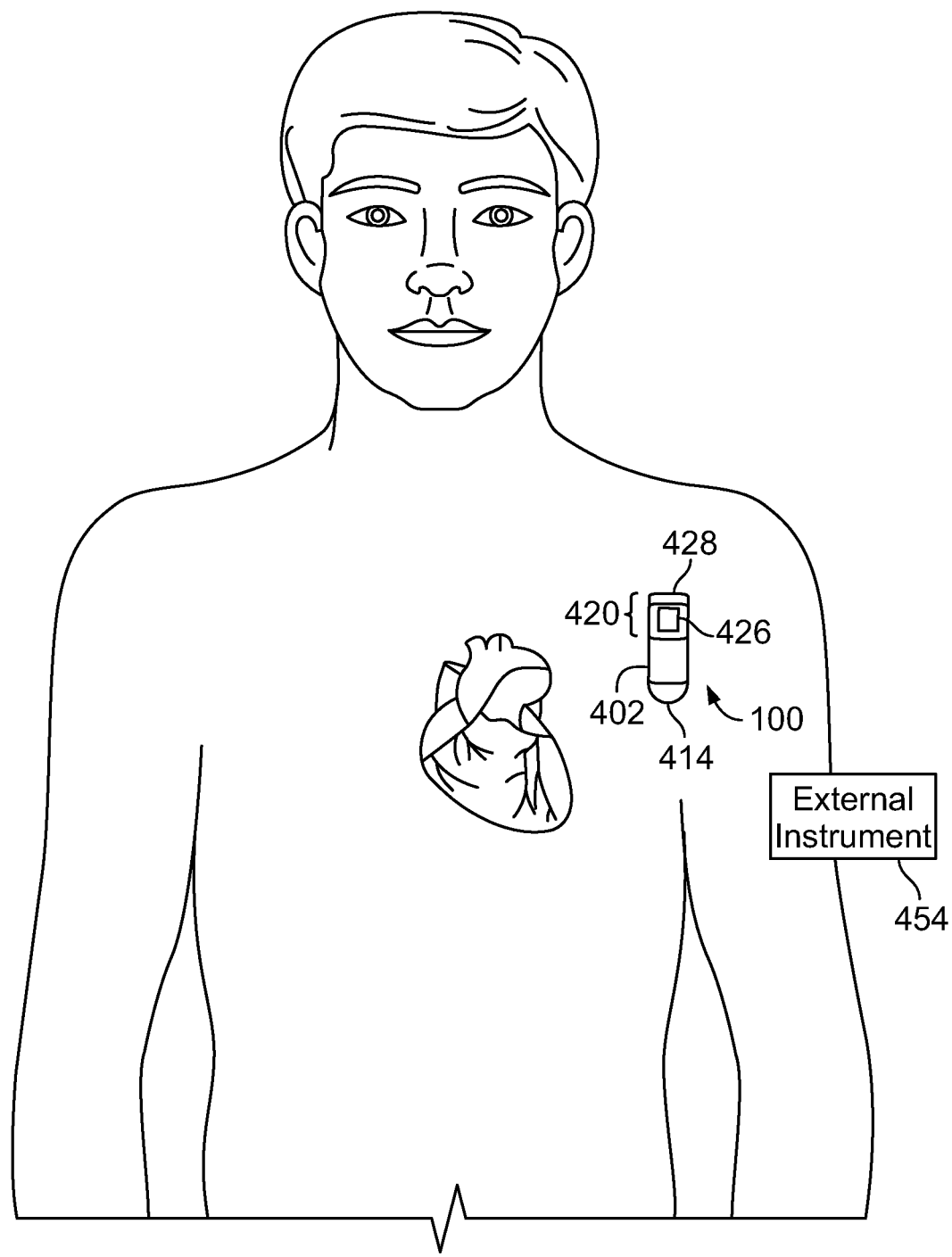
FIG. 4 illustrates an ICM intended for subcutaneous implantation at a site near the heart in accordance with embodiments herein.

FIG. 4 illustrates an ICM 400 intended for subcutaneous implantation at a site near the heart. The ICM 400 includes a pair of spaced-apart sense electrodes 414, 426 positioned with respect to a housing 402. The sense electrodes 414, 426 provide for detection of far field electrogram signals. Numerous configurations of electrode arrangements are possible. For example, the electrode 414 may be located on a distal end of the ICM 400, while the electrode 426 is located on a proximal side of the ICM 400. Additionally or alternatively, electrodes 426 may be located on opposite sides of the ICM 400, opposite ends or elsewhere. The distal electrode 414 may be formed as part of the housing 402, for example, by coating all but a portion of the housing with a nonconductive material such that the uncoated portion forms the electrode 414. In this case, the electrode 426 may be electrically isolated from the housing 402 electrode by placing it on a component separate from the housing 402, such as the header 420. Optionally, the header 420 may be formed as an integral portion of the housing 402. The header 420 includes an antenna 428 and the electrode 426. The antenna 428 is configured to wirelessly communicate with an external device 454 in accordance with one or more predetermined wireless protocols (e.g., Bluetooth, Bluetooth low energy, Wi-Fi, etc.). The housing 402 includes various other components such as: sense electronics for receiving signals from the electrodes, a microprocessor for processing the signals in accordance with algorithms, such as the AF detection algorithm described herein, a loop memory for temporary storage of CA data, a device memory for long-term storage of CA data upon certain triggering events, such as AF detection, sensors for detecting patient activity and a battery for powering components.

In at least some embodiments, the ICM 400 is configured to be placed subcutaneously utilizing a minimally invasive approach. Subcutaneous electrodes are provided on the housing 402 to simplify the implant procedure and eliminate a need for a transvenous lead system. The sensing electrodes may be located on opposite sides of the device and designed to provide robust episode detection through consistent contact at a sensor-tissue interface. The ICM 400 may be configured to be activated by the patient or automatically activated, in connection with recording subcutaneous ECG signals.

The ICM 400 senses far field, subcutaneous CA signals, processes the CA signals to detect arrhythmias and if an arrhythmia is detected, automatically records the CA signals in memory for subsequent transmission to an external device. The CA signal processing and AF detection is provided for, at least in part, by algorithms embodied in or implemented by the microprocessor. The ICM 400 includes one or more processors and memory that stores program instructions directing the processors to implement AF detection utilizing an on-board R-R interval irregularity (ORI) process that analyzes cardiac activity signals collected over one or more sensing channels.

Figure 5:
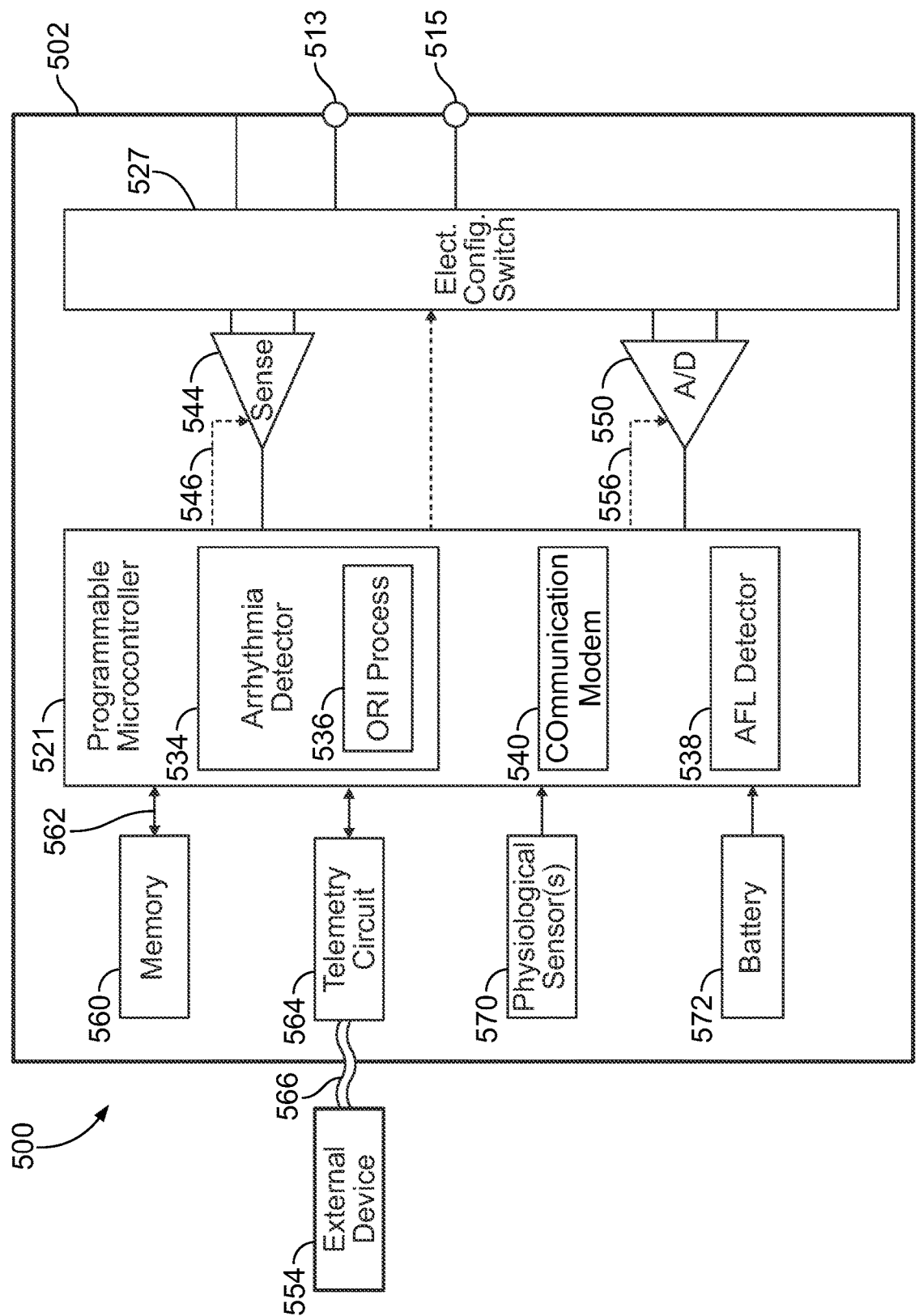
FIG. 5 shows a block diagram of the ICM formed in accordance with embodiments herein.

FIG. 5 shows a block diagram of the ICM 400 formed in accordance with embodiments herein. The ICM 400 may be implemented to monitor ventricular activity alone, or both ventricular and atrial activity through sensing circuit. Housing 502 further includes a connector (not shown) with at least one terminal 513 and optionally additional terminals 515. The terminals 513, 515 may be coupled to sensing electrodes that are provided upon or immediately adjacent the housing 502. Optionally, more than two terminals 513, 515 may be provided in order to support more than two sensing electrodes, such as for a unipolar and/or bipolar sensing scheme. The type and location of each electrode may vary.

The ICM 400 includes a programmable microcontroller 521 that controls various operations of the ICM 400, including cardiac monitoring. Microcontroller 521 includes a microprocessor (or equivalent control circuitry), RAM and/or ROM memory, logic and timing circuitry, state machine circuitry, and I/O circuitry. The microcontroller 521 also performs the operations described herein in connection with collecting cardiac activity data and analyzing the cardiac activity data.

A switch 527 is optionally provided to allow selection of different electrode configurations under the control of the microcontroller 521. The electrode configuration switch 527 may include multiple switches for connecting the desired electrodes to the appropriate I/O circuits, thereby facilitating electrode programmability. Microcontroller 521 includes an arrhythmia detector 534 that is configured to analyze cardiac activity signals to identify potential arrhythmia episodes (e.g., Tachycardias, Bradycardias, Asystole, Brady pause, atrial fibrillation, etc.). By way of example, the arrhythmia detector 534 may implement an arrhythmia detection algorithm as described in U.S. Pat. No. 8,135,456, the complete subject matter of which is incorporated herein by reference. The arrhythmia detector 534 analyzes sensed far field CA signals sensed along a sensing vector between a combination of subcutaneous electrodes for one or more beats. The arrhythmia detector 534 identifies one or more features of interest from the CA signals and based on further analysis of the features of interest determines whether the CA signals are indicative of a normal sinus rhythm or an arrhythmia episode. When an arrhythmia episode is identified, the arrhythmia detector 534 generates one or more DD markers that are temporally aligned with corresponding features of interest in the CA signals. The arrhythmia detector 534 forms a DCA data set associated with the classified arrhythmia episode and stores the DCA data set in the memory of the IMD. The arrhythmia detector 534 iteratively or periodically repeats the analysis of incoming far field CA signals to continuously add DCA data sets for respective arrhythmia episodes, thereby forming a collection of DCA data sets.

The ICM 400 is further equipped with a communication modem (modulator/demodulator) 540 to enable wireless communication. In one implementation, the communication modem 540 uses high frequency modulation, for example using RF, Bluetooth or Bluetooth Low Energy telemetry protocols. The signals are transmitted in a high frequency range and will travel through the body tissue in fluids without stimulating the heart or being felt by the patient. A sensing circuit 544 is selectively coupled to one or more electrodes that perform sensing operations, through the switch 527 to detect cardiac activity data indicative of cardiac activity. The sensing circuit 544 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the features of interest. In one embodiment, switch 527 may be used to determine the sensing polarity of the cardiac signal by selectively closing the appropriate switches. The output of the sensing circuit 544 is connected to the microcontroller 521 which, in turn, determines when to store the cardiac activity data of CA signals (digitized by the A/D data acquisition system 550) in the memory 560. The sensing circuit 544 receives a control signal 546 from the microcontroller 521 for purposes of controlling the gain, threshold, polarization charge removal circuitry (not shown), and the timing of any blocking circuitry (not shown) coupled to the inputs of the sensing circuit. The sensing circuit 544 may operate in a unipolar sensing configuration or in a bipolar sensing configuration.

The ICM 400 further includes an analog-to-digital ND data acquisition system (DAS) 550 coupled to one or more electrodes via the switch 527 to sample cardiac activity signals across any pair of desired electrodes. The data acquisition system 550 is configured to acquire cardiac electrogram (EGM) signals as CA signals, convert the raw analog data into digital data, and store the digital data as CA data for later processing and/or telemetric transmission to an external device 554 (e.g., a programmer, local transceiver, or a diagnostic system analyzer). The data acquisition system 550 is controlled by a control signal 556 from the microcontroller 521. The EGM signals may be utilized as the cardiac activity data that is analyzed for potential arrhythmia episodes.

By way of example, the external device 554 may represent a bedside monitor installed in a patient's home and utilized to communicate with the ICM 400 while the patient is at home, in bed or asleep. The external device 554 may be a programmer used in the clinic to interrogate the ICM 400, retrieve data and program detection criteria and other features. The external device 554 may be a handheld device (e.g., smartphone, tablet device, laptop computer, smartwatch and the like) that can be coupled over a network (e.g., the Internet) to a remote monitoring service, medical network and the like. The external device 554 facilitates access by physicians to patient data as well as permitting the physician to review real-time CA signals while collected by the ICM 400.

The microcontroller 521 is coupled to a memory 560 by a suitable data/address bus 562. The programmable operating parameters used by the microcontroller 521 are stored in memory 560 and used to customize the operation of the ICM 400 to suit the needs of a particular patient. Such operating parameters define, for example, detection rate thresholds, sensitivity, automatic features, AF detection criteria, activity sensing or other physiological sensors, and electrode polarity, etc. In addition, the memory 560 stores the cardiac activity data, as well as the markers and other data content associated with detection of arrhythmia episodes. The operating parameters of the ICM 400 may be non-invasively programmed into the memory 560 through a telemetry circuit 564 in telemetric communication via communication link 566 with the external device 554. The telemetry circuit 564 allows intracardiac electrograms and status information relating to the operation of the ICM 400 (as contained in the microcontroller 521 or memory 560) to be sent to the external device 554 through the established communication link 566. In accordance with embodiments herein, the telemetry circuit 564 conveys the DCA data sets and other information related to arrhythmia episodes to an external device.

The ICM 400 can further include one or more physiologic sensors 570. Such sensors are commonly referred to (in the pacemaker arts) as "rate-responsive" or "exercise" sensors. The physiological sensor 570 may further be used to detect changes in the physiological condition of the heart, or diurnal changes in activity (e.g., detecting sleep and wake states). Signals generated by the physiological sensors 570 are passed to the microcontroller 521 for analysis and optional storage in the memory 560 in connection with the cardiac activity data, markers, episode information and the like. While shown as being included within the housing 502, the physiologic sensor(s) 570 may be external to the housing 502, yet still be implanted within or carried by the patient. Examples of physiologic sensors might include sensors that, for example, activity, temperature, sense respiration rate, pH of blood, ventricular gradient, activity, position/posture, minute ventilation (MV), and so forth.

A battery 572 provides operating power to all of the components in the ICM 400. In alternate embodiments, the battery 572 could be rechargeable. See for example, U.S. Pat. No. 7,294,108, Cardiac event micro-recorder and method for implanting same, which is hereby incorporated by reference.

Figure 6:
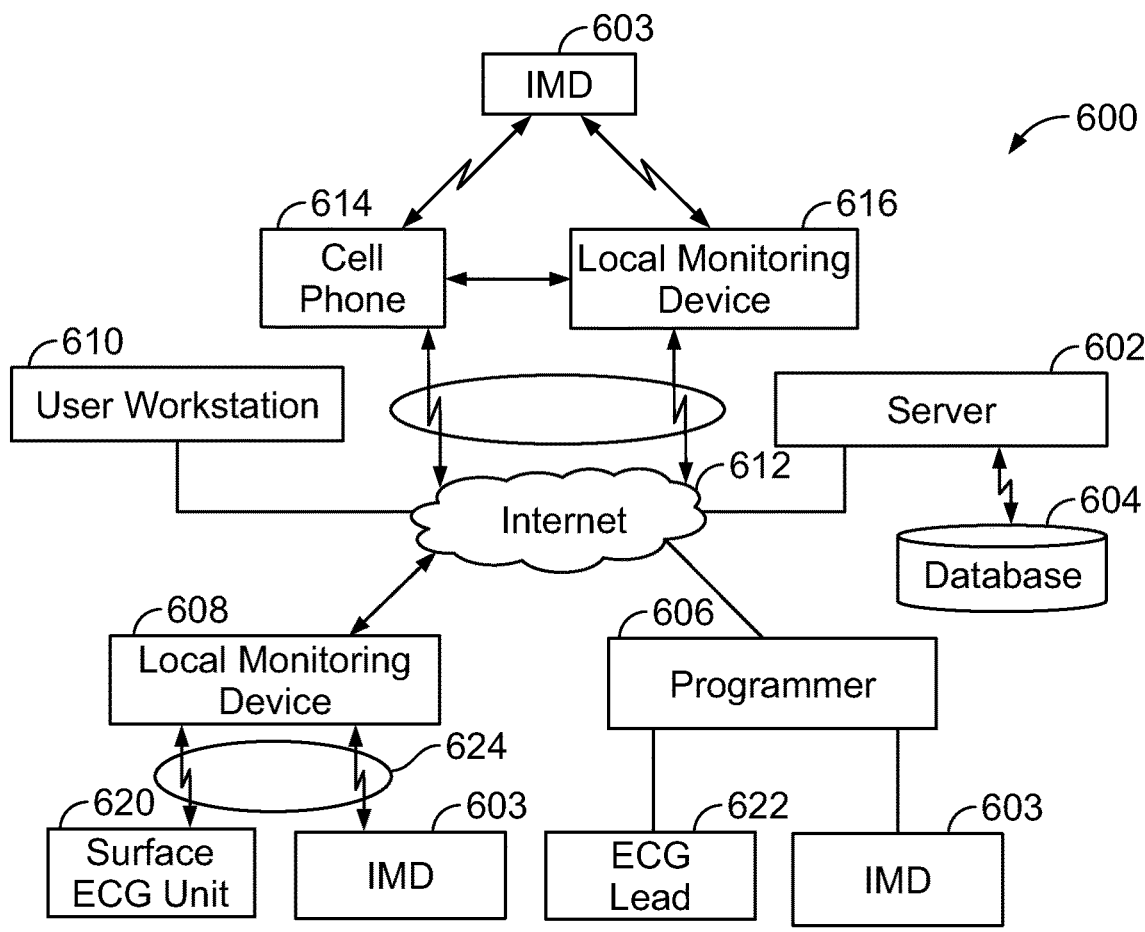
FIG. 6 illustrates a distributed processing system in accordance with embodiments herein.

FIG. 6 illustrates a distributed processing system 600 in accordance with embodiments herein. The distributed processing system 600 includes a server 602 connected to a database 604, a programmer 606, a local monitoring device 608 (e.g., IMD) and a user workstation 610 electrically connected to a network 612. Any of the processor-based components in FIG. 6 (e.g., workstation 610, cell phone 614, local monitoring device 616, server 602, programmer 606) may perform the processes discussed herein.

The network 612 may provide cloud-based services over the internet, a voice over IP (VoIP) gateway, a local plain old telephone service (POTS), a public switched telephone network (PSTN), a cellular phone-based network, and the like. Alternatively, the communication system may be a local area network (LAN), a medical campus area network (CAN), a metropolitan area network (MAN), or a wide area network (WAM). The communication system serves to provide a network that facilitates the transfer/receipt of data and other information between local and remote devices (relative to a patient). The server 602 is a computer system that provides services to the other computing devices on the network 612. The server 602 controls the communication of information such as DCA data sets, CA signals, motion data, bradycardia episode information, asystole episode information, arrythmia episode information, markers, heart rates, and device settings. The server 602 interfaces with the network 612 to transfer information between the programmer 606, local monitoring devices 608, 616, user workstation 610, cell phone 614 and database 604. For example, the server 602 may receive DCA data sets from various clinics, medical networks, individual patient's and the like and utilize the DCA data sets to train new ML models, update existing versions of ML models and add further outputs to existing and new ML models. The server 602 may further push new ML models and/or updated versions of ML models to various other devices, such as the programmers, local monitoring devices, cell phones, workstations and the like. The database 604 stores information such as DCA data sets, arrythmia episode information, arrythmia statistics, diagnostics, DD markers, CA signal, heart rates, device settings, and the like, for a patient population, as well as separated for individual patients, individual physicians, individual clinics, individual medical networks and the like. The server 602 may implement the machine learning training operations described in connection with The database 604 also maintains the machine learning models trained and updated as described herein. The machine learning models and other information are downloaded into the database 604 via the server 602 or, alternatively, the information is uploaded to the server 602 from the database 604. The programmer 606 may reside in a patient's home, a hospital, or a physician's office. The programmer 606 may wirelessly communicate with the IMD 603 and utilize protocols, such as Bluetooth, GSM, infrared wireless LANs, HIPERLAN, 3G, satellite, as well as circuit and packet data protocols, and the like. Alternatively, a telemetry "wand" connection may be used to connect the programmer 606 to the IMD 603. The programmer 606 is able to acquire ECG 622 from surface electrodes on a person (e.g., ECGs), electrograms (e.g., EGM) signals from the IMD 603, and/or CA data, arrythmia episode information, arrythmia statistics, diagnostics, markers, CA signal waveforms, atrial heart rates, device settings from the IMD 603. The programmer 606 interfaces with the network 612, either via the internet, to upload the information acquired from the surface ECG unit 620, or the IMD 603 to the server 602.

The local monitoring device 608 interfaces with the communication system to upload to the server 602 one or more of the DCA data sets, CA signals, motion data, arrythmia episode information, arrythmia statistics, diagnostics, markers, heart rates, sensitivity profile parameter settings and detection thresholds. In one embodiment, the surface ECG unit 620 and the IMD 603 have a bi-directional connection 624 with the local RF monitoring device 608 via a wireless connection. The local monitoring device 608 is able to acquire surface ECG signals from an ECG lead 622, as well as DCA CA data sets and other information from the IMD 603. On the other hand, the local monitoring device 608 may download the data and information discussed herein from the database 604 to the IMD 603.

The user workstation 610, cell phone 614 and/or programmer 606 may be utilized by a physician or medical personnel to interface with the network 612 to download DCA data sets, CA signals, motion data, and other information discussed herein from the database 604, from the local monitoring devices 608, 616, from the IMD 603 or otherwise. Once downloaded, the user workstation 610 may process the DCA data sets, CA signals and motion data in accordance with one or more of the operations described above. The user workstation 610, cell phone 614 and/or programmer 606, may be used to present information concerning at least one of the valid subset are invalid subset of the DCA data sets to a physician. Additionally or alternatively, the user workstation 610, cell phone 614 and/or programmer 606 may be utilized to display, in connection with each DCA data set, at least one of: i) a confidence indicator indicative of a degree of confidence that the corresponding DCA data set represents a true positive or false positive designation of an arrhythmia of interest; ii) a confidence indicator indicative of an accuracy of R-wave sensing implemented by the IMD; iii) a recommendation indicative of a sensitivity level to be utilized by the IMD to identify R waves in the CA signals; or iv) an output indicating that a particular DCA data set is unduly noisy and should not be characterized as a normal sinus rhythm, nor an arrhythmia.

The user workstation 610, cell phone 614 and/or programmer 606 may upload/push settings (e.g., sensitivity profile parameter settings), IMD instructions, other information and notifications to the cell phone 614, local monitoring devices 608, 616, programmer 606, server 602 and/or IMD 603. For example, the user workstation 610 may provide instructions to the IMD 603 in order to update sensitivity profile parameter settings when the IMD 603 determines that the motion data is indicative of at least one of a posture change or a respiration cycle that reduced the amplitude of the CA signals by an amount sufficient to cause the COI to exceed the COI limit.

The processes described herein may be performed by one or more of the devices illustrated in FIG. 6, including but not limited to the IMD 603, programmer 606, local monitoring devices 608, 616, user workstation 610, cell phone 614, and server 602. The process described herein may be distributed between the devices of FIG. 6. For example, one or more of the devices illustrated in FIG. 6 may include memory to store specific executable instructions and one or more of the pseudo SG model and/or arrhythmia prediction model. One or more of the devices illustrated in FIG. 6 may further include a display configured to present treatment notifications and/or other information.

Additionally or alternatively, the one or more characteristic of interest represent at least one of R-wave amplitude, R-wave amplitude variability, P-wave amplitude, P-wave amplitude variability, T-wave amplitudes, T-wave amplitude variability, RR interval amplitudes, RR interval amplitude variability, QRS area under the curve amplitudes, or QRS area under the curve amplitude variability, and the like. Additionally or alternatively, the CA signals represent subcutaneous electrocardiogram (EGM) signals for a series of beats over a predetermined period of time, the one or more processors configured to identify the one or more features of interest based in part on the CA signals. One or more of the external devices in FIG. 6 include the memory and the one or more processors and a transceiver, the transceiver configured to wirelessly receive the DCA data sets from the IMD.

The system of FIG. 6 further comprises one or more processors configured to execute the specific executable instructions to: obtain CA signals collected by an implantable medical device (IMD), wherein the COI, in the CA signals, exhibits a physiologic behavior; and apply the ML model to the CA signals to identify a risk factor that a patient will experience the arrhythmia at a future point in time even though the COI, in the CA signals, exhibits a physiologic behavior. The one or more processors are configured to train the pseudo CA signal model by: obtaining, for a reference collection of beats, both of first and second collections of CA signals collected along first and second sensing vectors utilizing first and second combinations of sensing electrodes, respectively; and training the pseudo CA signal model to convert the first collection of CA signals to a corresponding collection of pseudo CA signals associated with the second sensing vector and second combination of sensing electrodes. The one or more processors are further configured to include an arrhythmia risk prediction model configured to utilize machine learning trained to predict, as the risk factor, the risk that the patient will experience a ventricular arrhythmia.

Figure 7:
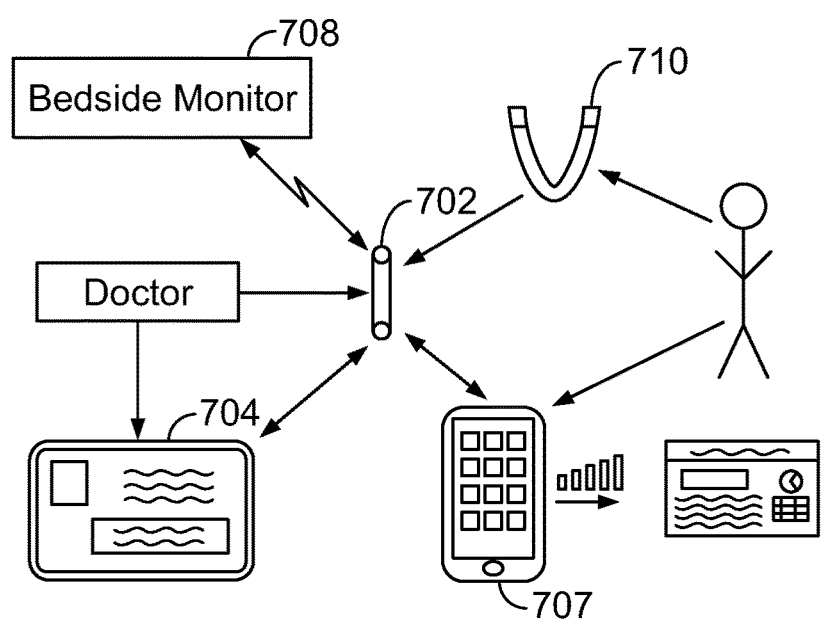
FIG. 7 illustrates a system level diagram indicating potential devices and networks that utilize the methods and systems in accordance with embodiments herein.

FIG. 7 illustrates a system level diagram indicating potential devices and networks that utilize the methods and systems herein. For example, an IMD 702 may be utilized to collect CA signals. The IMD 702 may supply the CA signals as well as sensitivity levels and motion data, to various local external devices, such as a tablet device 704, a smart phone 706, a bedside monitoring device 708, a smart watch and the like. The devices 704-708 include a display to present the various types of the CA signals, DD markers, statistics (e.g., % valid, % invalid), diagnostics, recommendations for adjustments in IMD sensing/therapy parameters and other information described herein. The IMD 702 may convey the CA signals and/or risk factor over various types of wireless communications links to the devices 704, 706 and 708. The IMD 702 may utilize various communications protocols and be activated in various manners, such as through a Bluetooth, Bluetooth low energy, Wi-Fi or other wireless protocol.

Further, embodiments herein are not limited to CNN type machine learning models, but instead to be utilized with other machine learning models. For example, embodiments herein may train and utilize another machine learning model called a "gradient boosted decision tree" to classify asystole SEGMs. Embodiments herein combine both the firmware and machine learning discriminators into an optimal system for determination of risk factors.

IMDs and Processes for Inclusion with Alternative Embodiments

Embodiments may be implemented in connection with one or more implantable medical devices (IMDs). Nonlimiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. The IMD may measure electrical and/or mechanical information. For example, the IMD may include one or more structural and/or functional aspects of the device(s) described in U.S. Pat. No. 9,333,351, entitled "NEUROSTIMULATION METHOD AND SYSTEM TO TREAT APNEA" issued May 10, 2016 and U.S. Pat. No. 9,044,610, entitled "SYSTEM AND METHODS FOR PROVIDING A DISTRIBUTED VIRTUAL STIMULATION CATHODE FOR USE WITH AN IMPLANTABLE NEUROSTIMULATION SYSTEM" issued Jun. 2, 2015, which are hereby incorporated by reference. The IMD may monitor transthoracic impedance, such as implemented by the CorVue algorithm offered by St. Jude Medical. Additionally or alternatively, the IMD may include one or more structural and/or functional aspects of the device(s) described in U.S. Pat. No. 9,216,285, entitled "LEADLESS IMPLANTABLE MEDICAL DEVICE HAVING REMOVABLE AND FIXED COMPONENTS" issued Dec. 22, 2015 and U.S. Pat. No. 8,831,747, entitled "LEADLESS NEUROSTIMULATION DEVICE AND METHOD INCLUDING THE SAME" issued Sep. 9, 2014, which are hereby incorporated by reference. Additionally or alternatively, the IMD may include one or more structural and/or functional aspects of the device(s) described in U.S. Pat. No. 8,391,980, entitled "METHOD AND SYSTEM FOR IDENTIFYING A POTENTIAL LEAD FAILURE IN AN IMPLANTABLE MEDICAL DEVICE" issued Mar. 5, 2013 and U.S. Pat. No. 9,232,485, entitled "SYSTEM AND METHOD FOR SELECTIVELY COMMUNICATING WITH AN IMPLANTABLE MEDICAL DEVICE" issued Jan. 5, 2016, which are hereby incorporated by reference. Additionally or alternatively, the IMD may be a subcutaneous IMD that includes one or more structural and/or functional aspects of the device(s) described in U.S. application Ser. No. 15/973,195, entitled "SUBCUTANEOUS IMPLANTATION MEDICAL DEVICE WITH MULTIPLE PARASTERNAL-ANTERIOR ELECTRODES" filed May 7, 2018; U.S. application Ser. No. 15/973,219, entitled "IMPLANTABLE MEDICAL SYSTEMS AND METHODS INCLUDING PULSE GENERATORS AND LEADS" filed May 7, 2018; U.S. Application Ser. No. 15/973,249, entitled "SINGLE SITE IMPLANTATION METHODS FOR MEDICAL DEVICES HAVING MULTIPLE LEADS", filed May 7, 2018, which are hereby incorporated by reference in their entireties. Further, one or more combinations of IMDs may be utilized from the above incorporated patents and applications in accordance with embodiments herein. Embodiments may be implemented in connection with one or more subcutaneous implantable medical devices (S-IMDs). For example, the S-IMD may include one or more structural and/or functional aspects of the device(s) described in U.S. application Ser. No. 15/973,219, entitled "IMPLANTABLE MEDICAL SYSTEMS AND METHODS INCLUDING PULSE GENERATORS AND LEADS", filed May 7, 2018; U.S. application Ser. No. 15/973,195, entitled "SUBCUTANEOUS IMPLANTATION MEDICAL DEVICE WITH MULTIPLE PARASTERNAL-ANTERIOR ELECTRODES", filed May 7, 2018; which are hereby incorporated by reference in their entireties. The IMD may represent a passive device that utilizes an external power source, and entirely mechanical plan will device, and/or an active device that includes an internal power source. The IMD may deliver some type of therapy/treatment, provide mechanical circulatory support and/or merely monitor one or more physiologic characteristics of interest (e.g., PAP, CA signals, impedance, heart sounds).

Embodiments herein may be incorporated with the structure and functionality (e.g. detection and analysis of the corresponding types of biological signals and determinations of the corresponding types of non-physiologic conditions) described in any or all of the publications referenced herein, including the following: U.S. patent application Ser. No. 16/930,791, filed Jul. 16, 2020, and titled "METHODS, DEVICES AND SYSTEMS FOR HOLISTIC INTEGRATED HEALTHCARE PATIENT MANAGEMENT"; U.S. Patent Publication Number 2014/0275827, entitled "METHOD AND SYSTEM FOR DERIVING EFFECTIVENESS OF MEDICAL TREATMENT OF A PATIENT" published Sep. 18, 2014; U.S. Patent Publication Number 2014/0039238, entitled "SYSTEMS AND METHODS FOR CONTROLLING NEUROSTIMULATION OF ACUPUNCTURE SITES USING AN IMPLANTABLE CARDIAC RHYTHM MANAGEMENT DEVICE" published Feb. 6, 2014; U.S. Patent Publication Number 2013/0204147, entitled "ATRIAL FIBRILLATION DETECTION BASED ON PULMONARY ARTERY PRESSURE DATA" published Aug. 8, 2013; U.S. Patent Publication Number 2013/0116583, entitled "SYSTEMS AND METHODS FOR PREDICTING AND CORROBORATING PULMONARY FLUID OVERLOADS USING AN IMPLANTABLE MEDICAL DEVICE" published May 9, 2013; U.S. Patent Publication Number 2012/0089032, entitled "METHOD AND SYSTEM FOR DISCRIMINATING AND MONITORING ATRIAL ARRHYTHMIA BASED ON CARDIOGENIC IMPEDANCE" published Apr. 12, 2012; U.S. patent application Ser. No. 11/378,604, filed Mar. 16, 2006, of Kroll et al., entitled, "System and Method for Detecting Arterial Blood Pressure based on Aortic Electrical Resistance using an Implantable Medical Device," now U.S. Pat. No. 7,654,964; U.S. Patent Publication Number 2011/0125206, entitled "SINGLE CHAMBER IMPLANTABLE MEDICAL DEVICE FOR CONFIRMING ARRHYTHMIA THROUGH RETROSPECTIVE CARDIAC SIGNALS" published May 26, 2011; U.S. Patent Publication Number 2014/0221771, entitled "METHOD AND IMPLANTABLE SYSTEM FOR BLOOD-GLUCOSE CONCENTRATION MONITORING USING PARALLEL METHODOLOGIES" published Aug. 7, 2014; U.S. Patent Publication Number 2014/0058278, entitled "SYSTEMS AND METHODS FOR DETECTING ISCHEMIC EVENTS" published Feb. 27, 2014; U.S. Patent Publication Number 2013/0218036, entitled "METHODS AND SYSTEMS TO CORRELATE ARRHYTHMIC AND ISCHEMIC EVENTS" published Aug. 22, 2013; U.S. Patent Publication Number 2012/0197149, entitled "SYSTEM AND METHOD FOR DISTINGUISHING AMONG CARDIAC ISCHEMIA, HYPOGLYCEMIA AND HYPERGLYCEMIA USING AN IMPLANTABLE MEDICAL DEVICE" published Aug. 2, 2012; U.S. Patent Publication Number 2012/0065527, entitled "METHODS AND SYSTEMS FOR MONITORING ATRIAL STIFFNESS" published Mar. 15, 2012; U.S. Patent Publication Number 2012/0046528, entitled "SYSTEM AND METHOD FOR DETECTING AND TREATING CARDIOVASCULAR DISEASE" published Feb. 23, 2012; U.S. Patent Publication Number 2011/0004111, entitled "ISCHEMIA DETECTION USING INTRA-CARDIAC SIGNALS" published Jan. 6, 2011; U.S. Pat. No.

8,514,086, entitled "DISPLAYS FOR A MEDICAL DEVICE", issued Aug. 20, 2013; U.S. Patent Publication Number 2011/0256024, entitled "MODULAR ANALYTE MONITORING DEVICE", published Oct. 20, 2011; U.S. Patent Publication Number 2010/0198142, entitled "MULTIFUNCTION ANALYTE TEST DEVICE AND METHODS THEREFORE", published Aug. 5, 2010; U.S. Patent Publication Number 2011/0160544, entitled "SYSTEM AND METHOD FOR ANALYSIS OF MEDICAL DATA TO ENCOURAGE HEALTHCARE MANAGEMENT", published Jun. 30, 2011; U.S. Pat. No. 5,063,081, entitled "METHOD OF MANUFACTURING A PLURALITY OF UNIFORM MICROFABRICATED SENSING DEVICES HAVING AN IMMOBILIZED LIGAND RECEPTOR" issued Nov. 5, 1991; U.S. Pat. No. 7,419,821, entitled "APPARATUS AND METHODS FOR ANALYTE MEASUREMENT AND IMMUNOASSAY" issued Sep. 2, 2008; U.S. Patent Publication Number 2004/0018577, entitled "MULTIPLE HYBRID IMMUNOASSAYS" published Jan. 29, 2004; U.S. Pat. No. 7,682,833, entitled "IMMUNOASSAY DEVICE WITH IMPROVED SAMPLE CLOSURE" issued Mar. 23, 2010; U.S. Pat. No. 7,723,099, entitled "IMMUNOASSAY DEVICE WITH IMMUNO-REFERENCE ELECTRODE" issued May 25, 2010; Baj-Rossi et al. "FABRICATION AND PACKAGING OF A FULLY IMPLANTABLE BIOSENSOR ARRAY", (2013) IEEE, pages 166-169. U.S. Pat. No. 6,786,874, entitled "APPARATUS AND METHOD FOR THE COLLECTION OF INTERSTITIAL FLUIDS" issued Sep. 7, 2004; and U.S. Pat. No. 9,872,641, entitled "METHODS, DEVICES AND SYSTEMS RELATED TO ANALYTE MONITORING" issued Jan. 23, 2018; U.S. patent application Ser. No. 11/387,579, filed Mar. 23, 2006, of Koh, entitled "System and Method for Calibrating a Blood Oxygen Saturation Sensor for use with an Implantable Medical Device," now U.S. Pat. No. 8,099,146; U.S. patent application Ser. No. 11/267,665, filed Nov. 4, 2005, of Kil et al., entitled "System and Method for Measuring Cardiac Output via Thermal Dilution using an Implantable Medical Device with Thermistor Implanted in Right Ventricle," now abandoned; U.S. Patent Publication No. 2005/0215914, to Bornzin et al., entitled "System and Method for Evaluating Heart Failure Based on Ventricular End-Diastolic Volume using an Implantable Medical Device"; U.S. Pat. No. 5,800,467 to Park et al., entitled "Cardio-Synchronous Impedance Measurement System for an Implantable Stimulation Device;" U.S. patent application Ser. No. 11/100,189, filed Apr. 5, 2005, of Koh, entitled "System and Method for Detection of Respiration Patterns via Integration of Intracardiac Electrogram Signals," now U.S. Pat. No. 7,404,799; and in U.S. patent application Ser. No. 11/623,663, filed Jan. 16, 2007, of Zou et al., entitled "Sensor/Lead Systems for use with Implantable Medical Devices," now U.S. Pat. No. 8,388,670.

All references, including publications, patent applications and patents, cited herein are hereby incorporated by reference to the same extent as if each reference were individually and specifically indicated to be incorporated by reference and were set forth in its entirety herein.

Closing

The various methods as illustrated in the Figures and described herein represent exemplary embodiments of methods. The methods may be implemented in software, hardware, or a combination thereof. In various of the methods, the order of the steps may be changed, and various elements may be added, reordered, combined, omitted, modified, etc. Various of the steps may be performed automatically (e.g., without being directly prompted by user input) and/or programmatically (e.g., according to program instructions).

Various modifications and changes may be made as would be obvious to a person skilled in the art having the benefit of this disclosure. It is intended to embrace all such modifications and changes and, accordingly, the above description is to be regarded in an illustrative rather than a restrictive sense.

Various embodiments of the present disclosure utilize at least one network that would be familiar to those skilled in the art for supporting communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C# or C++, or any scripting language, such as Ruby, PHP, Perl, Python or TCL, as well as combinations thereof. The server(s) may also include database servers, including without limitation those commercially available from Oracle®, Microsoft®, Sybase®, SAS® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

All references, including publications, patent applications and patents, cited herein are hereby incorporated by reference to the same extent as if each reference were individually and specifically indicated to be incorporated by reference and were set forth in its entirety herein.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and physical characteristics described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

What is claimed is:

1. A system for determining an arrhythmia risk, comprising:
   memory to store specific executable instructions and a machine learning (ML) model trained to predict an arrhythmia with a characteristic of interest (COI) that exhibits a non-physiologic behavior, the ML model trained based on pseudo cardiac activity (CA) signals, the pseudo CA signals generated by a pseudo signal generator (SG) model based on actual first CA signals;
   one or more processors configured to execute the specific executable instructions to:
      obtain second CA signals collected by an implantable medical device (IMD), wherein the COI, in the second CA signals collected, exhibits a physiologic behavior; and
      apply the ML model to the second CA signals to identify a risk factor that a patient will experience the arrhythmia at a future point in time even though the COI from the second CA signals, exhibits the physiologic behavior.

2. The system of claim 1, further comprising the IMD, the IMD including at least one processor from the one or more processors configured to apply an arrhythmia detection algorithm to analyze the second CA signals over a series of beats to determine whether the COI exhibits a physiologic or non-physiologic behavior, the arrhythmia detection algorithm determining that the second CA signals are not indicative of the arrhythmia, while the ML model determines that the second CA signals indicate that the risk factor represents a first risk level that the patient will experience the arrhythmia within a future period of time, wherein the first CA signals and second CA signals are at least one of i) collected along different first and second sensing vectors or collected utilizing different first and second electrode configurations.

3. The system of claim 1, wherein the risk factor is indicative of at least one of: i) a scale ranging from low to high risk levels, ii) a time prediction indicating a period of time until the patient is likely to have the arrhythmia, iii) an arrhythmia severity, or iv) a confidence probability regarding accuracy of the risk factor.

4. The system of claim 1, further comprising the IMD, the IMD comprising:
   a combination of subcutaneous electrodes configured to collect the second CA signals; the IMD, including IMD memory configured to store program instructions; and
   one or more IMD processors configured to execute the program instructions to:
      analyze the second CA signals and based on the analysis declare arrhythmias episodes; and
      a transceiver configured to wirelessly transmit the second CA signals to an external device.

5. The system of claim 1, further comprising a server that includes the memory and the one or more processors, the memory configured to store the second CA signals and to apply the ML model to the second CA signals to identify the risk factor.

6. The system of claim 1, wherein the ML model further comprises the pseudo SG model, the pseudo SG model configured to utilize machine learning to generate the pseudo CA signals based on the actual first CA signals, the pseudo CA signals associated with a pseudo sensing vector, the actual CA signals collected along an actual sensing vector.

7. The system of claim 1, wherein the one or more processors are configured to train the pseudo SG model by:
   obtaining, for a reference collection of beats, both of first and second collections of the actual first CA signals collected along first and second sensing vectors utilizing first and second combinations of sensing electrodes, respectively; and
   training the pseudo SG model to convert the first collection of the actual first CA signals to a corresponding collection of the pseudo CA signals associated with the second sensing vector and second combination of sensing electrodes.

8. The system of claim 7, wherein the first combination of sensing electrodes and first sensing vector correspond to a transvenous configuration, while the second combination of sensing electrodes and second sensing vector correspond to a non-transvenous subcutaneous configuration, the pseudo CA signals artificially generated by the pseudo SG model to simulate a morphology of the actual first CA signals collected in connection with the non-transvenous subcutaneous configuration.

9. The system of claim 1, wherein the CA signals represent subcutaneous electrocardiogram (EGM) signals for a series of beats over a predetermined period of time, the COI corresponding to at least one of: i) R-R rate, ii) R-R interval variability, iii) P-P rate, iv) P-P interval variability iv) a P-wave occurrence, v) an R-wave occurrence, vi) ST segment level, vii) ST segment variability, or viii) the PQRST complex, the COI of the EGM signals exhibiting a physiologic behavior.

10. The system of claim 1, wherein the actual first CA signals are collected along a first sensing vector extending between actual electrodes arranged in a first electrode configuration, the first electrode configuration representing one of i) a non-transvenous configuration, ii) a transvenous leadless configuration, or iii) a transvenous lead-based configuration, wherein the pseudo CA signals correspond to at least one of a pseudo sensing vector or pseudo electrode configuration that differs from the corresponding first sensing vector or first electrode configuration, memory further comprises the pseudo SG model, the pseudo SG model configured to convert the actual first CA signals to the pseudo CA signals.

11. The system of claim 1, wherein the pseudo CA signals and the second CA signals correspond to at least one of a common sensing vector or common electrode configuration.

12. The system of claim 1, wherein the pseudo CA signals correspond to a pseudo sensing vector between pseudo sensing sites, and wherein the memory further comprises the pseudo SG model, the pseudo SG model configured to generate the pseudo CA signals with a morphology that corresponds to a morphology of potential CA signals if measured along the pseudo sensing vector between the pseudo sensing vector.

13. A computer implemented method, comprising:
under control of one or more processors configured with specific executable instructions,
providing a pseudo signal generator (SG) model configured to generate pseudo cardiac activity (CA) signals based on actual first CA signals;
providing a machine learning (ML) model trained, based on the pseudo CA signals, to predict an arrhythmia with a characteristic of interest (COI) that exhibits a non-physiologic behavior;
obtaining second CA signals collected by an implantable medical device (IMD), wherein the COI in the second CA signals, exhibits a physiologic behavior; and
applying the ML model to the second CA signals to identify a risk factor that a patient will experience the arrhythmia at a future point in time even though the COI from the second CA signals, exhibits the physiologic behavior.

14. The method of claim 13, further comprising:
A) at least one of:
i) collecting the first and second CA signals along different first and second sensing vectors or
ii) ii) utilizing different first and second electrode configurations to collect the first and second CA signals; and
B) applying an arrhythmia detection algorithm to analyze the second CA signals over a series of beats to determine whether the COI exhibits a physiologic or non-physiologic behavior, the arrhythmia detection algorithm determining that the second CA signals are not indicative of the arrhythmia, while the ML model determines that the second CA signals indicate that the risk factor represents a first risk level that the patient will experience the arrhythmia within a future period of time.

15. The method of claim 13, wherein the risk factor is indicative of at least one of: i) a scale ranging from low to high risk levels, ii) a time prediction indicating a period of time until the patient is likely to have the arrhythmia, iii) an arrhythmia severity, or iv) a confidence probability regarding accuracy of the risk factor.

16. The method of claim 13, wherein the ML model further comprises the pseudo SG model, the pseudo SG model configured to utilize machine learning to generate the pseudo CA signals based on the actual first CA signals, the pseudo CA signals associated with a pseudo sensing vector, the actual first CA signals collected along an actual sensing vector.

17. The method of claim 16, wherein the pseudo CA signals are artificially generated by the pseudo SG model to simulate a morphology of CA signals collected in connection with a non-transvenous subcutaneous configuration of sensing electrodes.

18. The method of claim 13, wherein the ML model includes an arrhythmia risk prediction model configured to utilize machine learning trained to predict, as the risk factor, the risk that the patient will experience a ventricular arrhythmia.

19. The method of claim 13, wherein the risk factor indicates a likelihood that the patient will experience the arrhythmia within a three month time period following a time when the CA signals are collected by the IMD.

20. The method of claim 13, further comprising:
collecting the actual first CA signals along a first sensing vector extending between actual electrodes arranged in a first electrode configuration, the first electrode configuration representing one of i) a non-transvenous configuration, ii) a transvenous leadless configuration, or iii) a transvenous lead-based configuration, wherein the pseudo CA signals correspond to at least one of a pseudo sensing vector or pseudo electrode configuration that differs from the corresponding first sensing vector or first electrode configuration; and
utilizing the pseudo SG model to convert the actual first CA signals to the pseudo CA signals.

21. The method of claim 13, wherein the pseudo CA signals and the second CA signals correspond to at least one of a common sensing vector or common electrode configuration.

22. The method of claim 13, wherein the pseudo CA signals correspond to a pseudo sensing vector between pseudo sensing sites, and wherein the memory further comprises the pseudo SG model, the pseudo SG model configured to generate the pseudo CA signals with a morphology that corresponds to a morphology of potential CA signals if measured along the pseudo sensing vector between the pseudo sensing vector.

* * * * *